United States Patent
Gagnon et al.

(10) Patent No.: US 8,877,904 B2
(45) Date of Patent: *Nov. 4, 2014

(54) CHROMATOGRAPHY PURIFICATION OF ANTIBODIES

(75) Inventors: Peter S. Gagnon, San Clemente, CA (US); Hong Chen, San Ramon, CA (US); Russ Frost, Concord, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/460,474

(22) Filed: Apr. 30, 2012

(65) Prior Publication Data

US 2012/0264915 A1  Oct. 18, 2012

Related U.S. Application Data

(62) Division of application No. 12/419,482, filed on Apr. 7, 2009, now Pat. No. 8,188,242.

(60) Provisional application No. 61/123,518, filed on Apr. 8, 2008.

(51) Int. Cl.
| | |
|---|---|
| *A23J 1/00* | (2006.01) |
| *C07K 14/00* | (2006.01) |
| *C07K 16/00* | (2006.01) |
| *C07K 17/00* | (2006.01) |
| *C07K 1/36* | (2006.01) |
| *B01D 15/36* | (2006.01) |
| *B01D 15/38* | (2006.01) |
| *C07K 16/06* | (2006.01) |
| *A61K 39/395* | (2006.01) |
| *C07K 1/14* | (2006.01) |

(52) U.S. Cl.
CPC ............... *C07K 16/065* (2013.01); *C07K 1/36* (2013.01); *B01D 15/36* (2013.01); *C07K 2317/24* (2013.01); *B01D 15/3847* (2013.01); *C07K 1/14* (2013.01); *A61K 39/39591* (2013.01); *C07K 2317/50* (2013.01)
USPC .......................................... 530/415; 530/416

(58) Field of Classification Search
None
See application file for complete search history.

(56) References Cited

U.S. PATENT DOCUMENTS

| | | | |
|---|---|---|---|
| 3,917,527 | A | 11/1975 | Shaltiel |
| 4,694,074 | A | 9/1987 | Uemura et al. |
| 5,502,022 | A | 3/1996 | Schwarz et al. |
| 5,652,348 | A | 7/1997 | Burton et al. |
| 5,719,269 | A | 2/1998 | Schwarz et al. |
| 5,789,578 | A | 8/1998 | Burton et al. |
| 5,935,442 | A | 8/1999 | Lihme et al. |
| 5,945,520 | A | 8/1999 | Burton et al. |
| 6,090,288 | A | 7/2000 | Berglund |
| 6,498,236 | B1 | 12/2002 | Lihme et al. |
| 6,610,630 | B2 | 8/2003 | Schwarz et al. |
| 6,919,436 | B2 | 7/2005 | Lihme et al. |
| 7,008,542 | B2 | 3/2006 | Belew et al. |
| 7,067,542 | B2 | 6/2006 | Schostarez et al. |
| 7,144,743 | B2 | 12/2006 | Boschetti et al. |
| 7,326,776 | B2 | 2/2008 | Boschetti et al. |
| 2003/0229212 | A1 | 12/2003 | Farher et al. |
| 2004/0115785 | A1 | 6/2004 | Fong et al. |
| 2004/0124149 | A1 | 7/2004 | Boschetti et al. |
| 2004/0214157 | A1 | 10/2004 | Burton et al. |
| 2005/0107594 | A1 | 5/2005 | Sun et al. |
| 2005/0136521 | A1 | 6/2005 | Shukla et al. |
| 2006/0175237 | A1 | 8/2006 | Carlsson et al. |
| 2006/0175238 | A1 | 8/2006 | Lautamo |
| 2007/0015143 | A1 | 1/2007 | Boschetti et al. |
| 2007/0215534 | A1 | 9/2007 | Thommes et al. |
| 2007/0251885 | A1 | 11/2007 | Korpela et al. |

FOREIGN PATENT DOCUMENTS

| | | |
|---|---|---|
| EP | 0276138 | 7/1988 |
| EP | 0276138 A2 | 7/1988 |
| WO | WO 96/09116 | 3/1996 |
| WO | WO 96/09116 A1 | 3/1996 |
| WO | WO 98/08603 | 3/1998 |
| WO | WO 98/08603 A1 | 3/1998 |
| WO | WO 99/65607 | 12/1999 |
| WO | WO 99/65607 A1 | 12/1999 |
| WO | WO 00/69872 | 11/2000 |
| WO | WO 00/69872 A2 | 11/2000 |
| WO | WO 01/38228 | 5/2001 |
| WO | WO 01/38228 A1 | 5/2001 |

OTHER PUBLICATIONS

Tanaka et al. "TPD, FTIR, and Molecular Adsorption studies of calcium hydroxyapatite surface modified with hexanoic and decanoic acids" J. Colloid and Interface Science, 214, 31-37 (1999).*
International Search Report and Written Opinion from PCT/US2009/039738, filed on Apr. 7, 2009; 11 pages.
Bakerbond ABx™ Bonded Silica Gel. MSDS No. Z7269. Apr. 12, 2007. Retrieved from <http://www.jtbaker.com/msds/englishhtml/z7269.htm> on May 28, 2009.
Beena, M.S. et al.; "Phenyl alanine, tryptophan immobilized chitosan beads as adsorbents for selective removal of immunoproteins"; 1994 *J. Biomater.*, vol. 8, No. 4, pp. 385-403.
Bischoff, R. et al.; "Isolation of Specific TRNAS Using an Ionic-Hydrophobic Mixed-Mode Chromatographic Matrix"; 1985, *Analytical Biochemistry*, vol. 151, pp. 526-533.
Burton, S.C. et al.; "Hydrophobic charge induction chromatography: salt independent protein adsorption and facile elution with aqueous buffers"; 1998, *Journal of Chromatography A*, vol. 814, pp. 77-81.

(Continued)

*Primary Examiner* — Daniel E Kolker
*Assistant Examiner* — James Rogers
(74) *Attorney, Agent, or Firm* — Kilpatrick Townsend & Stockton LLP

(57) ABSTRACT

Methods, kits and apparatuses for chromatography purification of antibodies are provided. In some embodiments, antibodies are purified by mixed mode chromatography that does not comprise hydroxyapatite (HT) or fluorapatite (FT). The mixed mode chromatography step is then followed by a HT/FT chromatography step.

15 Claims, 16 Drawing Sheets

(56) References Cited

OTHER PUBLICATIONS

Flurkey, William H.; "Hydrophobic Adsorption Chromatography of Peach Polyphenol Oxidase"; 1980, *Journal of Food Science*, vol. 45, No. 6, pp. 1622-1624.

Gagnon, Pete; "A Ceramic Hydroxyapatite-Based Purification Platform"; 2006, *BioProcess International*, pp. 50-60.

Gagnon, Pete; "The Protein A Paradigm: Can it be improved? Can it be replaced?"; 2007, *18th International IBC Conference on Antibody Development and Production*, 28 pages.

Gagnon, Pete; "Nonionic Polymer Enhancement of Aggregate Removal in Ion Exchange and Hydroxyapatite Chromatography"; 2007, *12th Annual Waterside Conference*, San Juan, Puerto Rico, 33 pages.

Ghose, Sanchayita et al.; "Protein Interactions in Hydrophobic Charge Induction Chromatography (HCIC)"; 2005, *Biotechnol. Prog.*, vol. 21, pp. 498-508.

Ghose, Sanchayita et al.; "Evaluation and comparison of alternatives to Protein A chromatography Mimetic and hydrophobic charge induction chromatographic stationary phases"; 2006, *Journal of Chromatography A*, vol. 1122, pp. 144-152.

Girot, Pierre et al.; "2-Mercapto-5-benzimidazolesutfonic acid: an effective multimodal ligand for the separation of antobodies"; 2004, *Journal of Chromatography B*, vol. 808, pp. 25-33.

Gu, Rong-Fang et al.; "Demonstration of simultaneous cation-exchange and reversed-phase mechanisms on a strong-acid cation-exchange column"; 2001, *Journal of Chromatography A*, vol. 919, pp. 21-28.

Guerrier, Luc et al.; "Chromatography of Monoclonal Immunoglobulins on Hydroxyapatite micro-cristals trapped within cross-linked agarose"; 1999 conference in Lyon, France, 1 page abstract.

Guerrier, Luc et al.; "A dual-mode approach to the selective separation of antibodies and their fragments"; 2001, *Journal of Chromatography B*, vol. 755, pp. 37-46.

Low, Duncan et al.; "Future of antibody purification"; 2007, *Journal of Chromatography B*, vol. 848, pp. 48-63.

Maloisel, Jean-Luc; "Multimodal Chromatography—Designed media libraries for new and old separation challenges"; 2007, *PDA Conference*, San Diego, CA., 42 pages.

McLaughlin, L.W.; "Mixed-mode chromatography of Nucleic Acids"; 1989, *Chemical Reviews*, vol. 89, pp. 309-319.

Noel, Rob; "Mixed Mode Ligands for Isolation of Antibodies"; 2007, LersoParkalle 42, Copenhagen, Denmark, 28 pages.

Robinson, Mitchell et al.; "Physical-Chemical Requirements for the Catalysis of Substrates by Lysosomal Phospholipase A"; 1983, *The Journal of Biological Chemistry*, vol. 258, No. 23, pp. 14371-14378.

Sasaki, Ikuharu et al; "Hydrophobic-Ionic Chromatography: Its Application to Purification of Procine Pancreas Enzymes"; 1979, *J. Biochem.*, vol. 86, pp. 1537-1548.

Sasaki, Ikuharu et al; "Hydrophobic-Ionic Chomatography: Its Application to Microbial Glucose Oxidase, Hyaluronidase, Cholesterol Oxidase, and Cholesterol Esterase"; 1982, *J. Biochem.*, vol. 91, pp. 1555-1561.

Sellick, Ian; "Chromatography Advisor #3: Economic Benefits of Protein A Alternatives"; 2005, *BioProcess International*, pp. 68-70.

Shukla, Abhinav A. et al.; "Downstream processing of monoclonal antibodies-Application of platform approaches"; 2007, *Journal of Chromatography B*, vol. 848, pp. 28-39.

Simmonds, Roger J. et al.; "Protein Chromatography on Adsorbents with Hydrophobic and Ionic Groups"; 1976, *Biochem. Journal*, vol. 157, pp. 153-159.

Simmonds, Roger J. et al.; "Protein Chromatography on Adsorbents with Hydrophobic and Ionic Groups"; 1977, *Biochem. Journal*, vol. 163, pp. 397-400.

Subramanian, Anuradha; "Chromatographic Purification of MAbs with Non-Affinity Supports"; 2005, *Chemical and Biomolecular Engineering Research and Publications*, 12 pages.

Sulkowski, Eugene et al.; "Interaction of Human Interferons with Immobilized Hydrophobic Amino Acids and Dipeptides"; 1976, *The Journal of Biological Chemistry*, vol. 251, No. 17, pp. 4381-5385.

Yon, Robert J.; "Chromatography of Lipophilic Proteins on Absorbents Containing Mixed Hydrophobic and Ionic Groups"; 1972, *Biochem. Journal*, vol. 126, pp. 765-767.

Yon, Robert J.; "Enzyme Purification by Hydrophobic Chromatography: an Alternative Approach Illustrated in the Purification of Aspartate Transcarbamoylase from Wheat Germ"; 1974, *Biochem. Journal*, vol. 137, pp. 127-130.

Beena, M.S. et al.; "Phenyl alanine, tryptophan immobilized chitosan beads as adsorbents for selective removal of immunoproteins"; 1994, *J. Biomater.*, vol. 8, No. 4, pp. 385-403.

Burton, S.C. et al.; "Hydrophobic charge induction chromatography: salt independent protein adsorption and facile elution with aqueous buffers"; 1998, *Journal of Chromatography A*, vol. 814, pp. 71-81.

Girot, Pierre et al.; "2-Mercapto-5-benzimidazolesulfonic acid: an effective multimodal ligand for the separation of antobodies"; 2004, *Journal of Chromatography B*, vol. 808, pp. 25-33.

Doellgast et al.; "Purification of Human IgA by Salt-Mediated Hydrophobic Chromatography"; *Immunochemistry*; 13:135-139 (1976).

Hahn et al.; "Hydrophobic interaction chromatography of proteins. II. Binding capacity, recovery and mass transfer properties"; *J. Chromatog. B*; 790:99-114.

Kubota et al.; "Adsorption and Desorption of Serum Proteins Using Cellulosic Affinity Membrane Modified with N-Acetyl-L-phenylalanine"; *Sep. Sci. Tech.*; 38(2):323-326 (2003).

Schubert et al.; "Comparison of ceramic hydroxy- and fluroapatite versus Protein A/G-based resins in the isolation of a recombinant human antibody from cell culture supernatant"; *J. Chromatag. A*; 1142:106-113 (2007).

\* cited by examiner

Polyacrylamide gel electrophoresis analysis of Macro-Prep t-Butyl H1C fractions
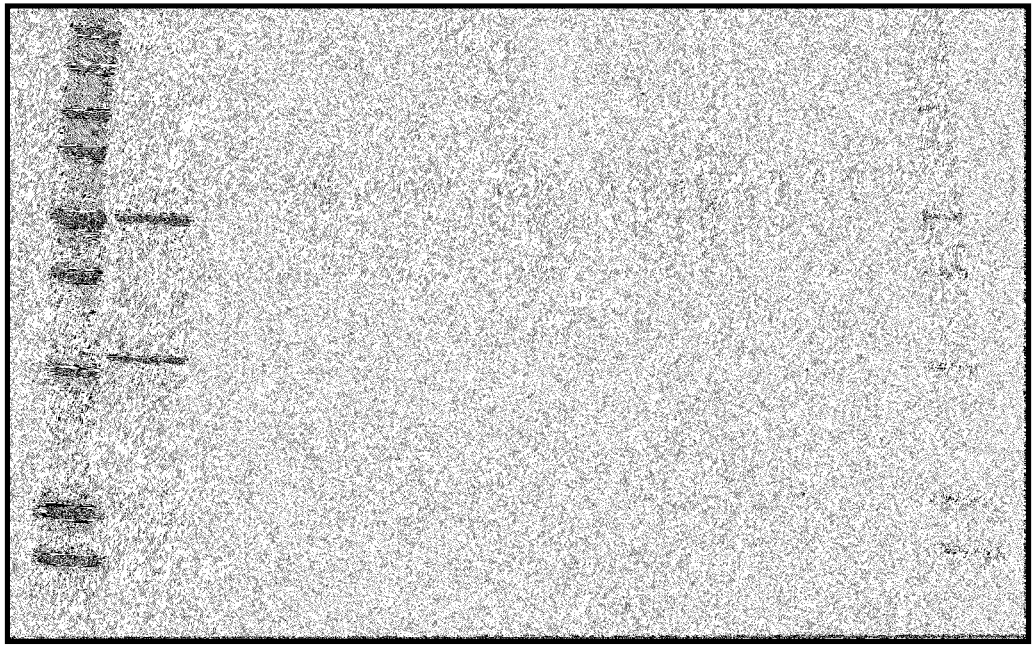
FIG. 8

CHROMATOGRAPHY PURIFICATION OF ANTIBODIES

CROSS-REFERENCE TO RELATED PATENT APPLICATIONS

The present application is a divisional patent application of U.S. patent application Ser. No. 12/419,482, filed Apr. 7, 2009, which claims benefit of priority to U.S. Provisional Patent Application No. 61/123,518, filed Apr. 8, 2008, each of which is incorporated by reference for all purposes.

BACKGROUND OF THE INVENTION

Mixed mode chromatography involves the use of solid phase chromatographic supports that employ multiple chemical mechanisms to adsorb proteins or other solutes. Examples include but are not limited to chromatographic supports that exploit combinations of two or more of the following mechanisms: anion exchange, cation exchange, hydrophobic interaction, hydrophilic interaction, hydrogen bonding, pi-pi bonding, and metal affinity. Mixed mode chromatography supports provide unique selectivities that cannot be reproduced by single mode chromatography methods such as ion exchange.

BRIEF SUMMARY OF THE INVENTION

The present invention provides for methods of purifying antibodies from a solution containing antibodies. In some embodiments, the methods comprise
   a. contacting a first solution containing antibodies to a mixed mode chromatography matrix, wherein the matrix does not include sulfur, thereby binding at least one antibody, e.g., a portion of the antibodies (e.g., at least 10%, 20%, 50%, 80%, 90% of the antibodies in the solution) to the matrix;
   b. separating the matrix with bound antibodies from the first solution;
   c. eluting the bound antibodies by changing the pH or salt concentration of solution in contact with the matrix and bound antibodies, thereby producing a solution comprising eluted antibodies;
   d. contacting the eluted antibodies to a solid support matrix, the solid support matrix comprising hydroxyapatite (HT) or fluorapatite (FT), wherein at least a portion (e.g., at least 10%, 20%, 50%, 80%, 90%) of the antibodies bind to the solid support matrix;
   e. separating the solid support matrix and bound antibodies from the second solution; and
   f. eluting the bound antibodies from the solid support matrix, thereby purifying the antibodies from the solution.

In some embodiments, the solution of eluted antibodies of step c is not substantially changed before step d.

In some embodiments, the contacting step a comprises binding the antibodies to the mixed mode matrix at a pH below 7. In some embodiments, the matrix comprises charged moieties at a pH below 7.

In some embodiments, the contacting step a comprises binding the antibodies to the matrix at a pH at or above 7.

In some embodiments, the contacting step a comprises binding the antibodies to the matrix in the presence of at least 1 M salt. In some embodiments, the contacting step a comprises binding the antibodies to the matrix in the presence of 1 M salt or less. In some embodiments, for example, less than 0.5 M or less than 0.25 M is used.

In some embodiments, the eluting step (c) comprises changing the salt concentration of the solution in contact with the matrix and bound antibodies, thereby eluting the antibodies.

In some embodiments, the eluting step (c) comprises changing the pH of the solution in contact with the matrix and bound antibodies, thereby eluting the antibodies. In some embodiments, the pH is changed from a pH below pH 7 to a pH above pH 7.

In some embodiments, the eluting step (f) comprises changing the salt concentration, thereby eluting the antibodies.

In some embodiments, the mixed mode chromatography matrix comprises a mixed mode ligand comprising an alkyl acid comprising between 4-10 carbons.

In some embodiments, the mixed mode ligand comprises hexanoic acid.

In some embodiments, the mixed mode chromatography matrix comprises a mixed mode ligand comprising phenylalanine. In some embodiments, the amine of the phenylalanine is acetylated or otherwise capped.

In some embodiments, wherein the mixed mode chromatography matrix comprises a mixed mode ligand comprises a t-butyl ether derivative of polymethacrylate.

In some embodiments, the methods further comprise an anion exchange chromatography step, a cation exchange, hydrophobic interaction or an ultrafiltration step, precipitation step, crystallization step, or liquid:liquid phase partitioning.

In some embodiments, the eluting step c comprises increasing the pH of the solution in contact with the matrix and bound antibodies.

In some embodiments, the solid support matrix comprises ceramic hydroxyapatite (CHT). In some embodiments, the solid support matrix comprises ceramic fluoroxyapatite (CFT).

The present invention also provides an apparatus for purifying antibodies. In some embodiments, the apparatus comprises,
   a first column tube and a second column tube, wherein the first and second column tubes comprise inlets and outlets, wherein the outlet of the first column tube connects to the inlet of the second column tube such that the first column tube is in fluid communication with the second column tube,
   wherein the first column tube contains a mixed mode chromatography matrix, wherein the matrix does not include sulfur, and the second column tube contains a solid support matrix, the solid support matrix comprising hydroxyapatite (HT) or fluorapatite (FT).

In some embodiments, the mixed mode chromatography matrix comprises a mixed mode ligand comprising an alkyl acid comprising between 4-10 carbons.

In some embodiments, the mixed mode ligand comprises hexanoic acid.

In some embodiments, the mixed mode chromatography matrix comprises a mixed mode ligand comprising phenylalanine. In some embodiments, the amine of the phenylalanine is acetylated or otherwise capped.

In some embodiments, the mixed mode chromatography matrix comprises a mixed mode ligand comprises a t-butyl ether derivative of polymethacrylate.

In some embodiments, the solid support matrix comprises ceramic hydroxyapatite (CHT). In some embodiments, the solid support matrix comprises ceramic fluoroxyapatite (CFT).

The present invention also provides kits for purifying antibodies. In some embodiments, the kit comprising,
a mixed mode chromatography matrix, wherein the matrix does not include sulfur; and
a solid support matrix, the solid support matrix comprising hydroxyapatite (HT) or fluorapatite (FT).
In some embodiments, the kits further comprise
a first column tube or cartridge comprising the mixed mode chromatography matrix; and
a second column tube or cartridge comprising the HT or FT solid support matrix.

In some embodiments, the first and second column tubes comprise inlets and outlets, wherein the outlet of the first column tube attachable to the inlet of the second column tube such that, when attached, the first column tube is in fluid communication with the second column tube.

In some embodiments, the mixed mode chromatography matrix comprises a mixed mode ligand comprising an alkyl acid comprising between 4-10 carbons.

In some embodiments, the mixed mode ligand comprises hexanoic acid.

In some embodiments, the mixed mode chromatography matrix comprises a mixed mode ligand comprising phenylalanine. In some embodiments, the amine of the phenylalanine is acetylated or otherwise capped.

In some embodiments, the mixed mode chromatography matrix comprises a mixed mode ligand comprises a t-butyl ether derivative of polymethacrylate.

In some embodiments, the solid support matrix comprises ceramic hydroxyapatite (CHT). In some embodiments, the solid support matrix comprises ceramic fluoroxyapatite (CFT).

DEFINITIONS

"Antibody" refers to an immunoglobulin, composite, or fragmentary form thereof. The term may include but is not limited to polyclonal or monoclonal antibodies of the classes IgA, IgD, IgE, IgG, and IgM, derived from human or other mammalian cell lines, including natural or genetically modified forms such as humanized, human, single-chain, chimeric, synthetic, recombinant, hybrid, mutated, grafted, and in vitro generated antibodies. "Antibody" may also include composite forms including but not limited to fusion proteins containing an immunoglobulin moiety. "Antibody" may also include antibody fragments such as Fab, F(ab')2, Fv, scFv, Fd, dAb, Fc and other compositions, whether or not they retain antigen-binding function.

"Mixed mode chromatography support" refers to a chromatographic solid phase that substantially involves a combination of two or more chemical mechanisms. Examples of chemical mechanisms that can be combined in mixed mode supports include but are not limited to cation exchange, anion exchange, hydrophobic interaction, hydrophilic interaction, hydrogen bonding, pi-pi bonding, and metal affinity. The solid phase can be a porous particle, nonporous particle, membrane, or monolith.

"Hydroxyapatite" refers to a mixed mode support comprising an insoluble hydroxylated mineral of calcium phosphate with the structural formula $Ca_{10}(PO_4)_6(OH)_2$. Its dominant modes of interaction are phosphoryl cation exchange and calcium metal affinity. Hydroxapatite is commercially available in various forms, including but not limited to ceramic, crystalline and composite forms. Composite forms contain hydroxyapatite microcrystals entrapped within the pores of agarose or other beads.

"Fluorapatite" refers to a mixed mode support comprising an insoluble fluoridated mineral of calcium phosphate with the structural formula $Ca_{10}(PO_4)_6F_2$. Its dominant modes of interaction are phosphoryl cation exchange and calcium metal affinity. Fluorapatite is commercially available in various forms, including but not limited to ceramic and crystalline composite forms.

"Ceramic" hydroxyapatite (CHT) or "ceramic" fluorapatite (CFT) refer to forms of the respective minerals in which nanocrystals are agglomerated into particles and fused at high temperature to create stable ceramic microspheres suitable for chromatography applications. Commercial examples of ceramic hydroxyapatite include, but are not limited to CHT Type I and CHT Type II. Commercial examples of fluorapatite include, but are not limited to CFT Type I and CFT Type II. Unless specified, CHT and CFT refer to roughly spherical particles of any average diameter, including but not limited to about 10, 20, 40, and 80 microns. The choice of hydroxyapatite or fluorapatite, the type, and average particle diameter can be determined by the skilled artisan.

BRIEF DESCRIPTION OF THE DRAWINGS

FIG. 8 illustrates a Coomassie brilliant blue stained, reduced, SDS PAGE gel loaded as discussed in the Examples.

DETAILED DESCRIPTION OF THE INVENTION

I. Introduction

Figure 1:
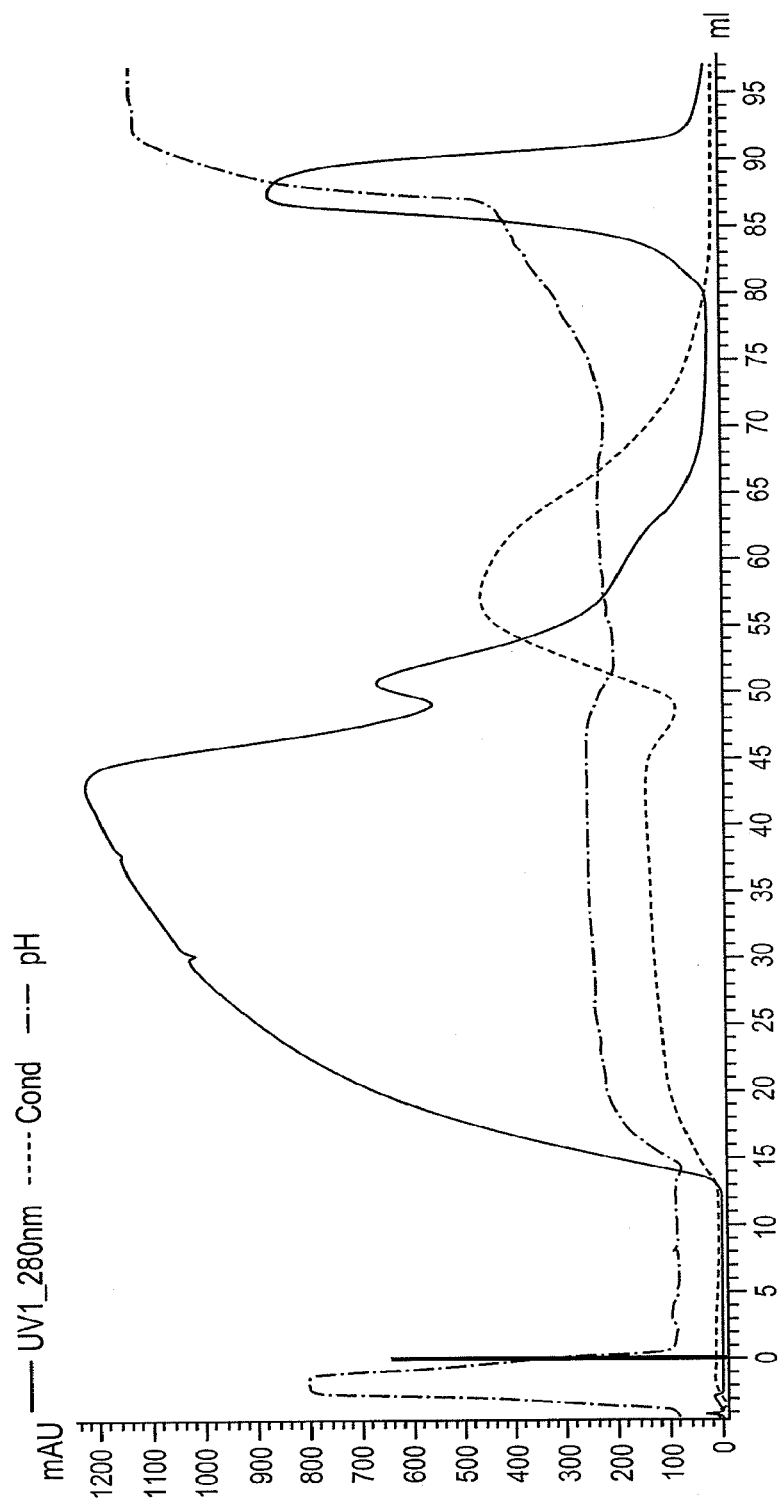
FIG. 1 illustrates a chromatogram from antibody capture from cell culture filtrate on UNOsphere Phenylalanine. The conductivity profile demonstrates that sample loading can be achieved at conductivity values corresponding more or less with physiological conditions, such as encountered in cell culture supernatants, and illustrates that antibody remains bound even when a wash with 1M NaCl is applied. The conductivity profile, in conjunction with the UV profile, further illustrates that the antibody can be eluted in a pH gradient at low conductivity to facilitate application of the eluted IgG to CHT or to an ion exhanger.

The present invention provides for purification of antibodies and other proteins using a variety of mixed mode chromatography reagents. A number of mixed mode ligands are described, including for example phenylalanine, alkyl acids, and t-butyl ether derivatives of polymethacrylate. It will be appreciated from the discussion herein that other types of mixed mode ligands can also be used to effectively purify antibodies and other proteins.

One aspect of the invention is the combination of a mixed mode chromatography step with a chromatography step using hydroxyapatite (HT) or fluorapatite (FT). This second step is useful for various "polishing" aspects, resulting in a highly purified final product without significant aggregates or cellular contaminants. Further, when used to purify antibodies, the combination of the mixed mode chromatography (not comprising HT/FT) with subsequent chromatography on HT or FT allows for a highly purified product that is produced at a fraction of the cost of the current industry standard for antibody purification, which involves antibody capture by affinity chromatography using Protein A chromatography media.

In some embodiments, the mixed mode step results in an eluate that can be added directly to the hydroxyapatite (HT) or fluorapatite (FT) chromatography media, thereby reducing the need for any sample manipulation during the purification process. This aspect is particularly valuable for large scale commercial purification of proteins, but is also convenient for smaller laboratory scale preparations.

Any antibody preparation can be used in the present invention, including unpurified or partially purified antibodies from natural, synthetic, or recombinant sources. Unpurified antibody preparations can come from various sources including, but not limited to, plasma, serum, ascites, milk, plant extracts, bacterial lysates, yeast lysates, or conditioned cell culture media. Partially purified preparations can come from unpurified preparations that have been processed by at least one chromatography, precipitation, other fractionation step, or any combination of the foregoing. In some embodiments, the antibodies have not been purified by protein A affinity prior to purification as described herein.

II. Mixed-Mode Chromatography

A. Ligands

The present invention provides for purification of antibodies using mixed mode chromatography, wherein the chromatography solid phase is not HT or FT, optionally combined with other purification steps that can include, for example, HT or FT chromatography.

Various mixed mode chromatography media are available commercially, any of which can be used to practice of this invention. Commercially available examples include but are not limited to MEP-Hypercel™, Capto-MMC™, Capto-Adhere™, and ABx™

In some embodiments, the mixed-mode chromatography support exploits a combination of anion exchange and hydrophobic interaction functionalities. Commercial examples of such supports include, but are not limited to, MEP-Hypercel™ and Capto Adhere™.

In some embodiments, the mixed-mode chromatography support exploits a combination of cation exchange and hydrophilic interaction functionalities. Commercial examples of such supports include, but are not limited to, Capto-MMCT™.

In some embodiments, the mixed-mode chromatography support exploits a combination of cation exchange, anion exchange, and hydrophobic interaction functionalities. Commercial examples of such supports include, but are not limited to, ABx™

In some embodiments, the mixed-mode chromatography support exploits a combination of anion exchange and hydrophobic interaction functionalities with potential for hydrogen bonding and pi-pi bonding. Commercial examples of such supports include, but are not limited to, Capto-Adhere™.

In some embodiments, the mixed-mode chromatography support exploits a combination of cation exchange and hydrophobic interaction functionalities with potential for hydrogen bonding and pi-pi bonding. Commercial examples of such supports include, but are not limited to, Capto-MMCT™.

Other non-commercial mixed mode media include, for example, mixed-mode chromatography support exploiting a combination of cation or anion exchange with hydrophobic interaction functionalities in the same ligand, or in a combination of ligands. Some examples of such ligands are described in, e.g., U.S. Pat. Nos. 7,008,542; 6,498,236; and 5,945,520.

In some embodiments, mixed-mode chromatography supports exploiting a combination of cation exchange with hydrophobic interaction functionalities can be used. For example, ligands comprising at least one acidic moiety such as a carboxyl group and also comprising at least one hydrophobic moiety such as a phenyl ring or an aliphatic hydrocarbon chain can be used.

In some embodiments, phenylalanine is covalently linked to a solid support. For example, the phenylalanine can be covalently linked to the solid support via the amine of phenylalanine. Phenylalanine can be linked to a solid support, for example, by nucleophilic replacement of a leaving group on the solid support, or by other chemistries known to those skilled in the art.

The secondary amino on the phenylalanine can be "capped" with an additional moiety to form a tertiary amide, thereby preventing or reducing the formation of cationic ammonium (and therefore formation of a zwitterion) at the pH at which the chromatography is performed. In some embodiments, the amine is capped with an acetyl group. Those of skill in the art will appreciate there are a number of ways to acetylate the amine. In some embodiments, the beads are dried and then exposed to acetyl chloride. In some embodiments the beads are submitted to solvent exchange with acetone, rather than drying, and then exposed to acetyl chloride.

In another embodiment, a t-butyl ether derivative of a polymethacrylate is used as the mixed mode ligand. An example of this type of derivative is Macro-Prep t-butyl HIC™, which is commercially available from Bio-Rad, Inc. (Hercules, Calif.). T-butyl ether derivatives can be formed from polymeric beads comprising (1) glycidyl methacrylate groups. For example, a fraction of the ester groups on the polymer backbone can be hydrolyzed to carboxylic acid groups while the reaction of t-butoxide proceeds with the epoxide. This is illustrated in the following diagram.

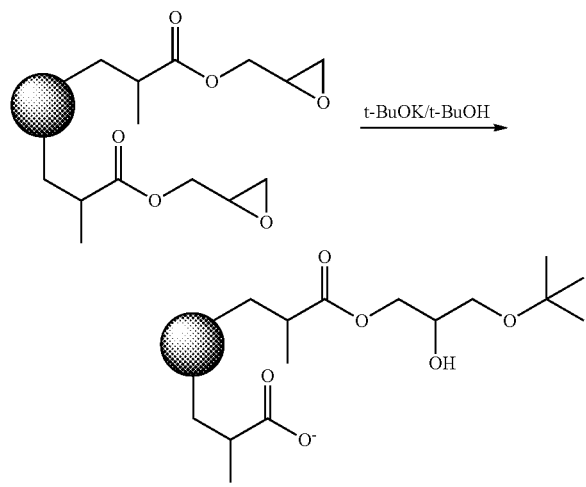

Macro-Prep t-Butyl HIC typically contains from 131-266 micromoles carboxyl groups/ml and 25-45 micromoles t-butyl groups/ml resin, though those of skill in the art will appreciate that the total amount and ratio of these two groups can be varied as desired.

In yet other embodiments, an alkyl acid (e.g., a carboxylic acid) is used as a mixed mode ligand. In some embodiments, the alkyl acid is an n-alkyl acid having between 4-10, 4-6, 4-8, 6-8, or 5-7 carbons, e.g., 2, 3, 4, 5, 6, 7, 8 carbons. As discussed in more detail in the examples, hexanoic acid can be used. Alternatively, in some embodiments, acetic acid, butanoic acid, octanoic acid, or decanoic acid are used.

Alkyl acids can be linked to a hydroxy-functionalized solid matrix. Halogenated alkyl acids can react directly with the hydroxy-functionalized solid matrix. For example, a bromoalkyl acid, such as 6-bromohexanoic acid, can be coupled to UNOsphere Diol. Reactions can be performed, e.g., with 1 M NaOH in the presence of excess bromoacid.

In yet another embodiment, Tosoh HIC media, which contains backbone carboxylate, similar to Macro-Prep t-Butyl HIC resin, is treated with NaOH, to form backbone carboxylates, producing a mixed mode similar to Macro-Prep t-Butyl HIC.

In some embodiments, the mixed mode matrix (i.e., the ligand or solid support) does not include sulfur.

Chromatography Conditions

As will be appreciated in the art, load, wash and elution conditions for use in the mixed mode chromatography of the invention will depend on the specific chromatography media/ligands used. Optimally, the antibodies are bound to the mixed mode resin, with only a pH adjustment, and without any adjustment of the antibody cell culture filtrate to minimize conductivity of the sample, in order to optimally bind antibody to the mixed mode resin.

In some embodiments, loading (i.e., binding the antibodies to the matrix), and optionally washing, is performed at a pH below 7, e.g., between 3-7, 4-7, 3-5, 4-5, 4-6, etc. A pH below 7 is of particular use where cationic/hydrophobic mixed mode ligands are employed. In some embodiments the matrix comprises charged moieties (e.g., negatively charged or positively charged) at a pH below 7.

In some embodiments, loading (i.e., binding the antibodies to the matrix), and optionally washing, is performed at a pH above 7, e.g., between 7-8, 7-9, etc. A pH at or above 7 is of particular use where anionic/hydrophobic mixed mode ligands are employed.

In some embodiments, loading (i.e., binding the antibodies to the matrix), and optionally washing, is performed in the presence of at least 1 M salt (e.g., sodium). In other embodiments, loading (i.e., binding the antibodies to the matrix), and optionally washing is performed in the presence of less than 1 M salt.

In embodiments employing mixed-mode chromatography supports exploiting a combination of cation exchange with hydrophilic interaction functionalities, it can be useful to load a sample onto a column, and subsequently wash the column, at a low pH (e.g., pH 3-5, e.g., 4-5). The desired protein (e.g., antibody) is then eluted by raising the pH, for example, above about pH 6. In some embodiments, the protein is eluted by raising the pH from the wash condition to a pH of at least 6.5, 7, or more, e.g., to about pH 7.2. In some of these embodiments, the salt concentrations are not substantially changed during the elution step. In some of these embodiments, the salt is maintained at a low concentration (e.g., below about 50 mM, e.g., below 20 mM, e.g., between 0-20 mM, e.g., 10 mM). Exemplary salts and buffer include, e.g., sodium phosphate, sodium acetate, potassium phosphate or potassium acetate. There are other acidic buffers that can be used for the binding to the mixed mode resin at low pH, including succinate and MES, both of which are compatible with subsequent application to CHT. Citrate could be used, but would have to be removed before application of eluted IgG to CHT.

Elution conditions resulting in a nearly neutral pH (e.g., pH 6-8, e.g., about pH 7) and low salt (e.g., 0-50 mM) are of particular use because the solution comprising the desired eluted protein can be subsequently loaded onto a CHT or CFT column or other solid support without substantially changing the solution. This allows for elimination of intervening steps such as dialysis or ultrafiltration that may otherwise be used before a second round of chromatography or other purification. "Substantially change" refers to no or less than 5% change in pH, salt conditions, and/or conductivity.

B. Support Matrices

A variety of support matrices can be used according to the present invention. Generally, the support matrix will be a hydrophilic polymer that allows for linkage of the ligand, optionally via a spacer.

In some embodiments, the base matrix is hydrophilic and in the form of a polymer, e.g. a polymer that is insoluble and more or less swellable in water. Suitable polymers are polyhydroxy polymers, e.g. based on polysaccharides, such as agarose, dextran, cellulose, starch, pullulan, etc. and completely synthetic polymers, such as polyacrylic amide, polymethacrylic amide, poly(hydroxyalkylvinyl ethers), poly(hydroxyalkylacrylates) and polymethacrylates (e.g.

polyglycidylmethacrylate), polyvinyl alcohols and polymers based on styrenes and divinylbenzenes, and copolymers in which two or more of the monomers corresponding to the above-mentioned polymers are included. Polymers, which are soluble in water, may be derivatized to become insoluble, e.g. by cross-linking and by coupling to an insoluble body via adsorption or covalent binding. Hydrophilic groups can be introduced on hydrophobic polymers (e.g. on copolymers of monovinyl and divinylbenzenes) by polymerisation of monomers exhibiting groups which can be converted to OH, or by hydrophilization of the final polymer, e.g. by adsorption of suitable compounds, such as hydrophilic polymers. In some embodiments, the support is an UNOsphere™ support, a polymer produced from water-soluble hydrophilic monomers (Bio-Rad, Hercules, Calif.). Alternatively, the matrix is agarose (GE Sepharose or Sterogene Superflow and Ultraflow).

III. HT/FT Chromatography Step

In some embodiments of the invention, HT or FT chromatography is performed on the antibodies after a previous mixed mode chromatography step that did not involve HT or FT. In some embodiments, the HT or FT is a ceramic HT or ceramic FT. Commercial examples of ceramic hydroxyapatite include, but are not limited to CHT Type I and CHT Type II. Commercial examples of fluorapatite include, but are not limited to CFT Type I and CFT Type II. Unless specified, CHT and CFT refer to roughly spherical particles of any average diameter, including but not limited to about 10, 20, 40, and 80 microns. The choice of hydroxyapatite or fluorapatite, the type, and average particle diameter can be determined by the skilled artisan. Other forms of HT are commercially available from, e.g., Bio-Rad, Pall Corp. and American International Chemical, Inc. A composite gel form of HT referred to as an "ultrogel" is commercially available from Pall Corp.

A variety of different loading, washing and elution conditions can be used, as desired. In some embodiments, the initial loading conditions are adapted such that the protein (e.g., antibody) eluted from the initial non-HT, non-FT mixed mode step is applied directly to the HT/FT column.

Elution can be achieved, for example, by changing the salt conditions in the liquid phase. For example, the salt and/or conductivity of the liquid phase is increased (linearly or stepwise) to a point that which the antibody elutes. Exemplary washing conditions include, e.g., 10 mM phosphate, pH 6.7, with elution achieved by increasing the salt concentration (step-wise or in a linear fashion) (e.g., to 10 mM phosphate, 1.5M NaCl, pH 6.7).

IV. General Chromatography Information

In preparation for contacting the antibody preparation with the mixed mode support, the chemical environment inside the column is typically equilibrated. This is commonly accomplished by flowing an equilibration buffer through the column to establish the appropriate pH; conductivity; identity, molecular weight, and concentration of nonionic organic polymer (discussed further below); and other pertinent variables.

In some embodiments, the antibody preparation is also equilibrated to conditions compatible with the column equilibration buffer before the invention can be practiced. This generally consists of adjusting the pH of the antibody preparation In some embodiments, after the column and antibody preparation is equilibrated, the antibody preparation may be contacted with the column. The antibody preparation may be applied at a linear flow velocity in the range of, for example, about 50-300 cm/hr. Appropriate flow velocity can be determined by the skilled artisan.

In some embodiments, the invention is practiced in a packed bed column, a fluidized/expanded bed column and/or a batch operation where the mixed mode support is mixed with the antibody preparation for a certain time.

In some embodiments, a mixed mode chromatography support is packed in a column.

In some embodiments, the mixed mode support is packed in a column of at least 5 mm internal diameter and a height of at least 25 mm. Such embodiments are useful, e.g., for evaluating the effects of various conditions on a particular antibody.

Another embodiment employs the mixed mode support, packed in a column of any dimension required to support preparative applications. Column diameter may range from less than 1 cm to more than 1 meter, and column height may range from less than 1 cm to more than 30 cm depending on the requirements of a particular application. Appropriate column dimensions can be determined by the skilled artisan.

After use, the mixed mode column may optionally be cleaned, sanitized, and stored in an appropriate agent, and optionally, re-used.

As desired, the solutions used in one or more of the load, wash or elution steps during the mixed mode and/or HT or FT chromatography step comprise a nonionic organic polymer. Optionally, nonionic polymers are only used during the HT/FT step and not during the prior mixed mode step. Examples of nonionic organic polymers include, but are not limited to polyethylene glycol (PEG), polypropylene glycol, cellulose, dextran, starch, and polyvinylpyrrolidone.

The presence of a nonionic organic polymer enhances binding capacity of antibody on HT or FT, thereby enabling higher levels of productivity to be achieved, and expanding the range of methods that may be considered. The presence of nonionic organic polymer also preferentially enhances the retention of antibody on HT or FT, in comparison to most contaminating proteins, thereby enabling novel selectivity for improved removal of non-antibody proteins. Further, the presence of nonionic organic polymer preferentially enhances retention of aggregated antibody and other very large molecules on HT or FT, in comparison to non-aggregated antibody, thereby enabling novel selectivity and superior separation performance for large-contaminant removal. PEG provides a general model for behavior of soluble nonionic organic polymers within the context of the invention. Thus, while PEG is discussed in the following text, one should recognize that the information applies equally to other nonionic polymers, including but not limited to those specifically listed herein.

The invention may be practiced with PEG with an average polymer molecular weight ranging from about 100 to about 10,000 Daltons. Exemplary PEG includes PEG having an average molecular weight of, e.g., 200, 300, 400, 500, 900, 1000, 1400, 2000, 3300, 4500, 8000, 10000, 14000, etc. In some embodiments, the PEG has an average weight between 400-1000, 200-1000, 400-2000, or 1000-5000. A wide variety of different PEGs are available from, e.g., Aldrich.

PEG or other organic polymers can be linear or branched polymers.

Lower molecular weight PEGs will generally require a higher concentration to achieve an effect similar to higher molecular weight PEGs.

Lower concentrations of a given molecular weight of PEG are generally used to enhance the binding of larger antibodies and fusion proteins compared to concentrations of PEG resulting in the same amount of enhanced binding of smaller proteins. For example, IgM, with an approximate molecular weight of about 960 kD, will generally require a lower concentration of PEG to achieve a certain degree of binding enhancement than IgG, with an approximate molecular weight of 160 kD. Retention of aggregates, complexes, and other large molecule contaminants will generally be enhanced to a greater degree than the unaggregated forms of the proteins from which they are derived.

Lower concentrations of PEG will be generally required to enhance the binding of molecules that are strongly retained by the mixed mode chromatography support, compared to the concentration for PEG to achieve the same enhanced binding for molecules that are weakly retained.

The effects described in the two preceding paragraphs will generally be compound: the retention of large molecules that are strongly retained in the absence of nonionic organic polymer will be enhanced more by application of the invention than molecules that are smaller and weakly retained, smaller and strongly retained, or larger and weakly retained.

In some embodiments, PEG with an average molecular weight of about 6,000 Daltons is employed in a concentration range from 0.0-7.5% to separate intact IgG from aggregated forms.

In some embodiments, PEG with an average molecular weight of about 2,000 Daltons is employed in a concentration range from 0.0-15.0% to separate intact IgG from aggregated forms.

The identity, appropriate average molecular weight, and concentration of the organic polymer to practice the invention can be determined by the skilled artisan.

V. Optional Additional Steps

The present invention may be combined with other purification methods to achieve higher levels of purification. Examples include, but are not limited to, other methods commonly used for purification of antibodies, such as protein A and other forms of affinity chromatography, anion exchange chromatography, cation exchange chromatography, hydrophobic interaction chromatography, immobilized metal affinity chromatography, and additional mixed mode chromatography methods. Other options, include, but are not limited to precipitation, crystallization, and/or liquid partitioning methods.

VI. Apparatus

The present invention provides apparatuses that are useful for carrying out the methods of the invention. For example, the present invention provides an apparatus for purifying antibodies, the apparatus comprising, a first column tube (or cartridge) and a second column tube (or cartridge), wherein the first and second column tubes comprise inlets and outlets, wherein the outlet of the first column tube connects to the inlet of the second column tube (either directly or indirectly through, e.g., a connector tube) such that the first column tube is in fluid communication with the second column tube, wherein the first column tube contains a mixed mode chromatography matrix and the second column tube contains a solid support matrix, the solid support matrix comprising hydroxyapatite (HT) or fluorapatite (FT). An apparatus with this configuration optionally allows for uninterrupted flow from the initial mixed mode chromatography column through top the HT/FT column. Optionally, various inlets and outlets can be included to allow for changing conditions (e.g., wash and elution solutions can be added via the inlets, test samples can be collected from outlets).

The apparatus can include any mixed mode support or ligands without limitation, e.g., as discussed above with respect to the method.

VII. Kits

Kits for use in purification of proteins (e.g., antibodies) are also provided. In some embodiments, the kits comprise: a mixed mode chromatography matrix; and/or a solid support matrix, the solid support matrix comprising hydroxyapatite (HT) or fluorapatite (FT). The above described matrices can be provided in the form of a reagent that can be packed into column(s) or can be packaged such that they can be packed in a separate column. Optionally, the kits will include separate columns to be packed at a time chosen by the user.

In some embodiments, the kits comprise a first column tube or cartridge comprising the mixed mode chromatography matrix; and a second column tube or cartridge comprising the solid support matrix. In some embodiments, the first and second column tubes comprise inlets and outlets, wherein the outlet of the first column tube can be connected to the inlet of the second column tube such that the first column tube is in fluid communication with the second column tube when connected the two tubes are connected.

In addition, the kits may include instructional materials containing directions (i.e., protocols) for the practice of the methods of this invention. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

Example 1

Production of Phenylalanine Ligand Column

UNOsphere chromatography media are based on water-soluble, hydrophilic acrylamido and vinylic monomers that are polymerized in the presence of porogens, to yield spherical particles (U.S. Pat. No. 6,423,666). UNOsphere Diol is a polymer produced with pendent diol groups, which can be used to produce a variety of functional media for use in lab-scale and process chromatography. UNOsphere Phenylalanine mixed mode resin was made from UNOsphere Diol base bead in two steps: (a) oxidation of UNOsphere Diol to UNOsphere Aldehyde; and (b) coupling of phenylalanine onto UNOsphere matrix via reductive amination. The amino group of phenylalanine becomes secondary after the reductive amination reaction. If needed, this secondary amino group can be acetylated to eliminate its protonation at acidic pHs. Coupling level of phenylalanine ligand is determined by acid-base titration.

A general scheme of the procedure is shown below:

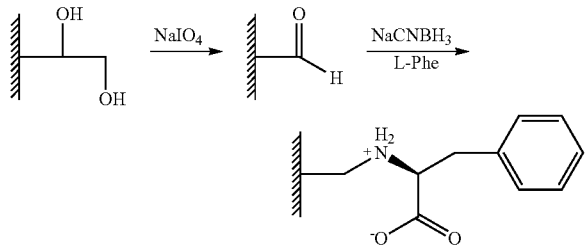

Detailed Procedures

Oxidation of UNOsphere Diol to UNOsphere Aldehyde. Wash 40 ml settled UNOsphere Diol resin with 400 ml×4 deionized water in a column. Transfer washed resin cake into a 250 ml polyethylene bottle. Add 100 ml of 0.2 M NaIa$_4$ solution into the bottle and mix the content head-to-head at ambient temperature with a rotator. After 1 hr of mixing, wash the resin with 400 ml×4 deionized water in a column.

Coupling of L-Phenylalanine onto UNOsphere Aldehyde via reductive amination. Dissolve 0.49 g of L-Phenylalanine in 25 ml of PBS at 70° C. Let the L-Phenylalanine solution cool to ambient temperature. Suspend 10 ml of UNOsphere Aldehyde resin cake in the L-Phenylalanine solution. Add 125 mg of NaCNBH$_3$ into the suspension and gently mix the suspension head-to-head overnight at ambient temperature with a rotator. Wash resin with 100 ml×4 deionized water in a column.

Determine ligand content. L-Phenylalanine ligand content can be determined using an acid-base titration method. Acidify 10 ml UNOsphere L-Phenylalanine resin with 1.0 N HCl, and then wash the resin with 100 ml×4 deionized water. Titrate the acidified resin with 0.10 N NaOH in a 0.20 ml increment until pH reaches 11.4. Repeat this process for 10 ml UNOsphere Diol resin. Use volume difference of titrant, 0.10 N NaOH, for these two resins to calculate ligand content. The ligand content is about 0.043 mmol of L-Phenylalanine per ml of resin.

Acetylation of secondary amino group. Wash 10 ml UNOsphere L-Phenylalanine resin from (c) with 100 ml×4 deionized water and 50 ml MeOH. Dry the resin in a vacuum oven at 60° C. under house vacuum overnight. Cool resin to ambient temperature and suspend it into 25 ml acetone (dried over molecular sieves). Cool the suspension to −10° C. and add slowly 78 µl diisopropylethylamine, followed by 32 µl acetyl chloride. Gently stir the reaction mixture at −5 to −10° C. for 35 minutes. Wash the resin with 50 ml acetone, 50 ml MeOH, and 100 ml×3 deionized water.

Example 2

Phenylalanine Ligand—Cation Exchange Mode

One mode of the invention can be referred to as "cation exchange mode" because the phenylalanine column is operated by exploiting the carboxylic acid group as a cation exchanger (though the hydrophobic portion of the phenylalanine continues to contribute to antibody interaction). The hydrophobic nature of the ligand allows good binding capacity (IgG uptake) by the media in the presence of higher amounts of salt (via a hydrophobic effect) than would usually be tolerated by traditional hydrophilic cation exchangers.

This specific example has been performed under the following conditions: 1 mL of phenylalanine UNOsphere was packed in a 5 mm×5 cm column and equilibrated with 5 column volumes (CV) 0.05M acetate buffer at pH 4.5, at a linear flow rate of 300 cm/hr. 15 mL of clarifed cell culture supernatant containing monoclonal chimeric IgG at about 1 mg/mL was titrated to pH 4.7 by gradual addition of 0.1 M acetic acid, then applied to the column. The column was washed with equlibration buffer until the UV profile returned to baseline. It was then washed with 5CV of 0.05 M acetate, 1 M NaCl, pH 4.5, then restored to equilibration buffer. The column was then eluted with a 15 CV linear gradient to 10 mM sodium phosphate buffer, pH 7.2. Results of the elution are shown in FIG. 1.

After initial fractionation on phenylalanine UNOsphere in either cation exchange or hydrophobic interaction mode, the eluted IgG was loaded onto hydroxyapatite (CHT type 1 40 micron) and eluted in a sodium chloride gradient as described in numerous recent Bio-Rad publications. This increases the purity of the antibody, particularly removing antibody aggregates, DNA, endotoxin, and virus. Conditions for the CHT chromatography are as follows.

CHT type 1, 40 µm. 1 mL 5 mm×5 cm, 300 cm/hr.
Buffer A: 10 mM sodium phosphate, pH 6.7.
Buffer B: 10 mM sodium phosphate, 1.5M NaCl, pH 6.7.
Buffer C: 500 mM sodium phosphate, pH 7.0.

Figure 2:
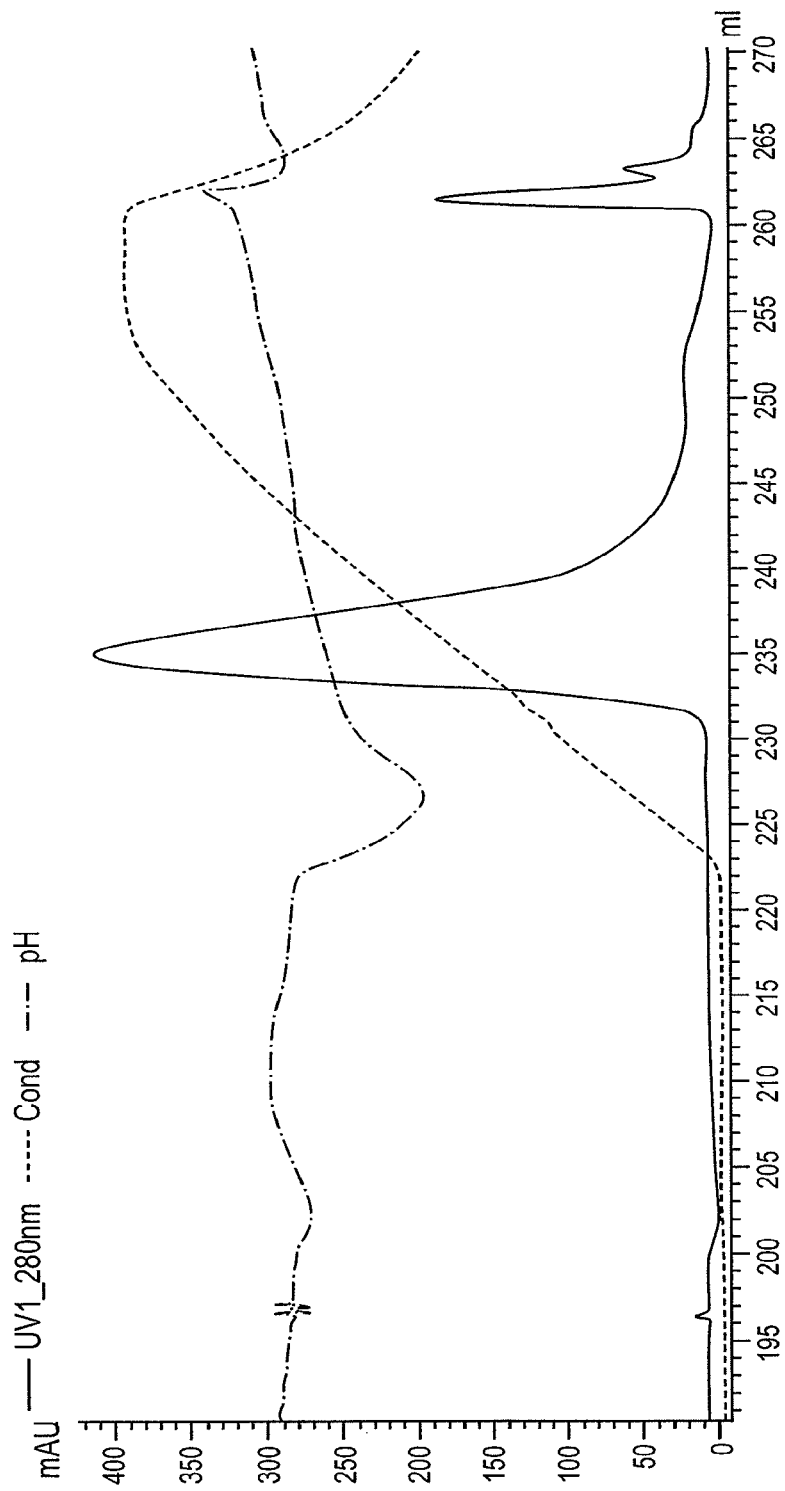
FIG. 2 is a chromatogram illustrating polishing purification of antibody eluted from UNOsphere Phenylalanine in FIG. 1 on hydroxyapatite. The reagents and conditions were as follows: CHT type 1, 40 μm, 1 mL 5 mm×5 cm, 300 cm/hr. Buffer A: 10 mM phosphate, pH 6.7. Buffer B: 10 mM phosphate, 1.5M NaCl, pH 6.7. Buffer C: 500 mM sodium phosphate, pH 7.0. EQ column with buffer A. The IgG eluate from the capture step on UNOsphere Phenylalanine was loaded onto the hydroxyapatite column, washed with buffer A, and eluted in a 30 CV linear gradient to buffer B. The column was cleaned with buffer C.

The column was equilibrated with buffer A. The antibody eluate from the UNOsphere phenylalanine chromatography was loaded and then washed with buffer A. Elution was achieved with a 30 CV linear gradient to buffer B. The column was then cleaned with buffer C. A chromatogram of the elution is shown in FIG. 2.

Figure 3:
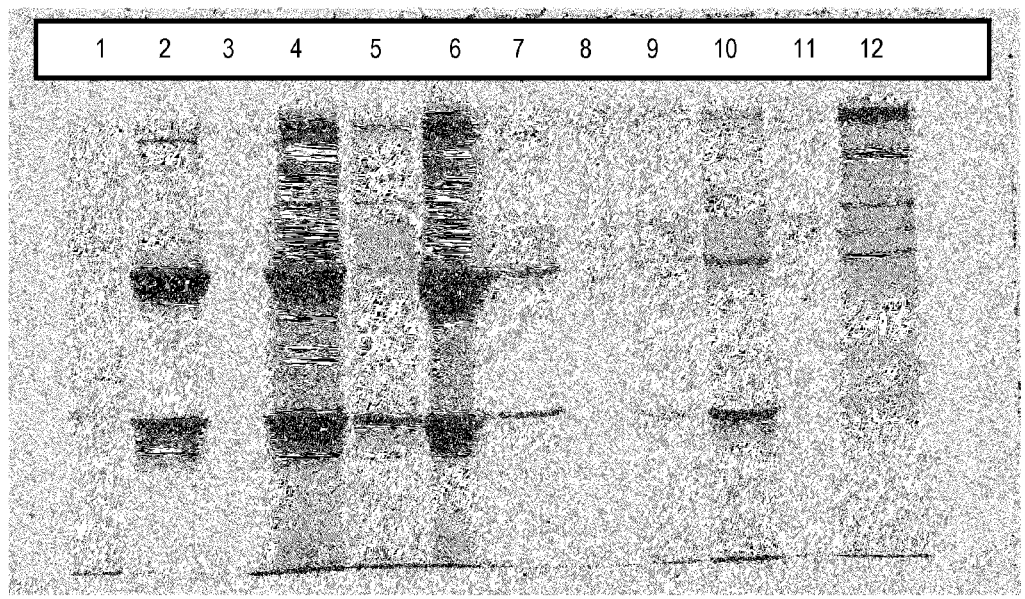
FIG. 3 is a Flamingo stained, reduced SDS-PAGE gel loaded as discussed in the Examples.

Samples at various stages of purification were loaded and analyzed on SDS-PAGE to monitor the purification process (FIG. 3).

Lane 4 represents the unpurified cell culture supernatant that was applied to the Phenylalanine column.

Lane 9 represents material that did not bind to the column when it was applied to the column. This would be material that corresponds to the peak running from about 15-45 mL on FIG. 1. The absence of a band corresponding to antibody heavy chain indicates that antibody is effectively bound by the column. A band corresponding roughly with antibody light chain suggests that the column supports selective removal of light chain.

Lane 5 represents later-eluting unbound material corresponding to the peak that occurs from about 45-53 mL on FIG. 1. This material is dominated by a band corresponding roughly with antibody light chain, and demonstrates that the column has a weak affinity for light chain, sufficient to retard its passage through the column, but not sufficient to bind it. This demonstrates that the column can be used for separation of free light chain and intact antibody, and suggests potential applications for purification of antibody fragments.

Lane 10 represents material eluted from phenylalanine resin in a high salt wash step, corresponding to about 53-65 mL on FIG. 1. The presence of heavy chain suggests some loss of antibody, but the dominance of light chain indicates that most of the loss is not intact antibody.

Lane 1 represents the leading shoulder on the elution peak, corresponding to about 80-85 mL on the Figure. It contains a trace of light chain but no significant concentration of intact antibody.

Lane 6 represents the main elution peak from phenylalanine resin, corresponding to about 85-92 mL on FIG. 1. It is dominated by the two peaks representing antibody heavy and light chain in proportions indicating intact antibody, which dominates the composition of the fraction overall. In combination with the chromatogram (FIG. 1), this shows that the column is effective in removing the majority of contaminants. The difference in composition between the two elution fractions (Lanes 5 and 6) suggest that elution conditions could be optimized to provide even higher purity. The column fraction corresponding to Lane 6 was carried forward to the CHT (hydroxyapatite step).

Lane 11 represents material that did not bind to the CHT column. This corresponds to the part of the chromatogram from about 205-220 mL (FIG. 2). Antibody content is nil, indicating good elimination of contaminants.

Lane 2 represents the primary elution peak from CHT, corresponding to about 232-240 mL. This peak typically corresponds with non-aggregated antibody, suggesting the utility of the combined techniques (phenylalanine and CHT) for supporting a high degree of purification, selective fractionation of antibody fragments from intact antibody, and selective fractionation of antibody aggregates from (intact) non-aggregated antibody.

Lane 7 represents the trailing peak from CHT, corresponding to about 245-260 mL. This peak typically corresponds with antibody aggregates when antibodies are fractionated under these conditions.

Lane 12 represents the cleaning peak from CHT, corresponding to about 26-264 mL on FIG. 2. The fraction is dominated by contaminants but appears to contain a small amount of antibody. Antibody occurring in this fraction is typically revealed to be highly aggregated.

Lanes 3 and 8 are blank.

Example 3

Effect of Capping of Phenylalanine Ligand

Figure 4:
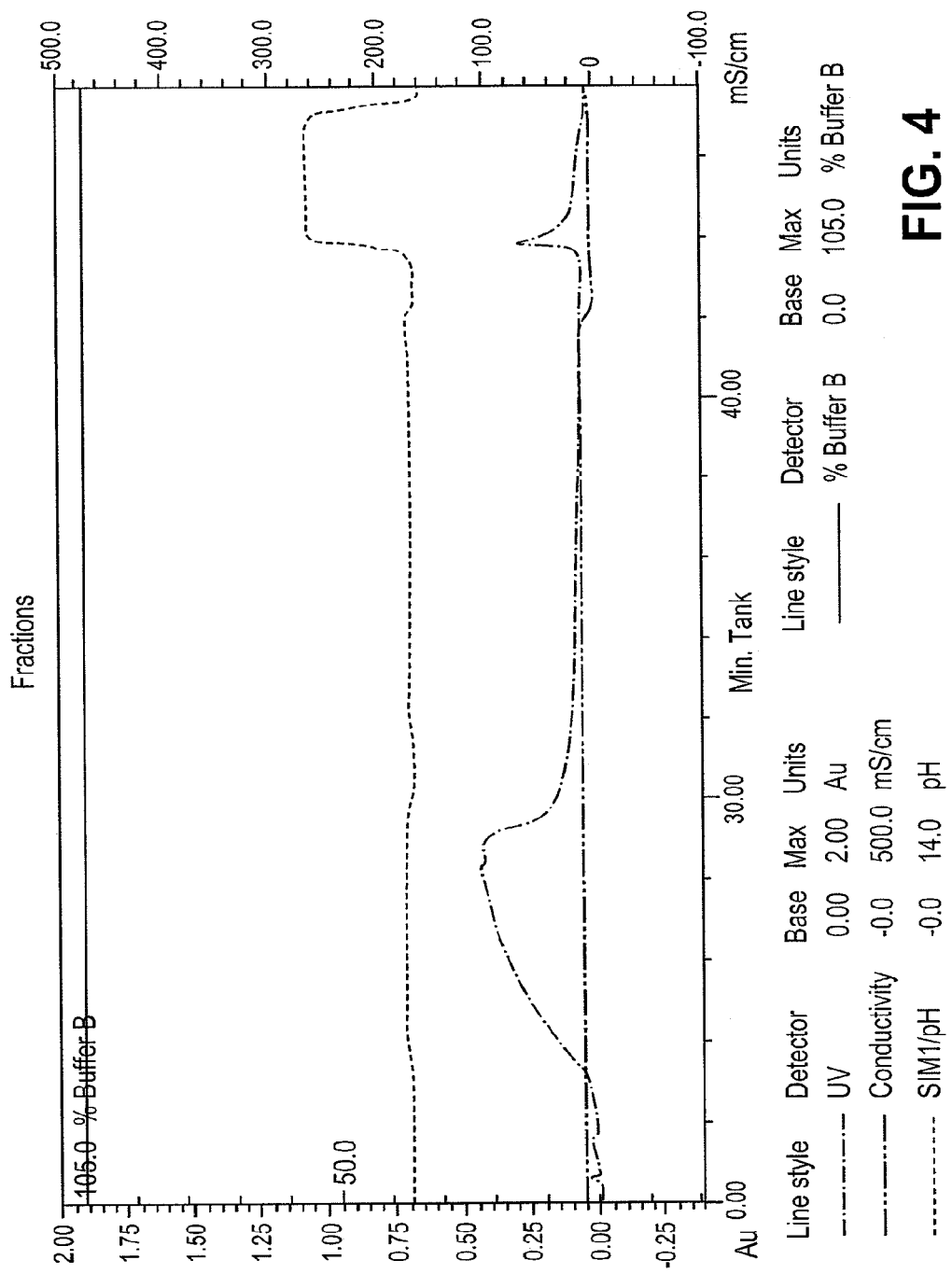
FIG. 4 is a chromatogram showing binding and elution of purified immunoglobulin from a non-acetylated phenylalanine UNOsphere resin as discussed in the Examples.
Figure 5A:
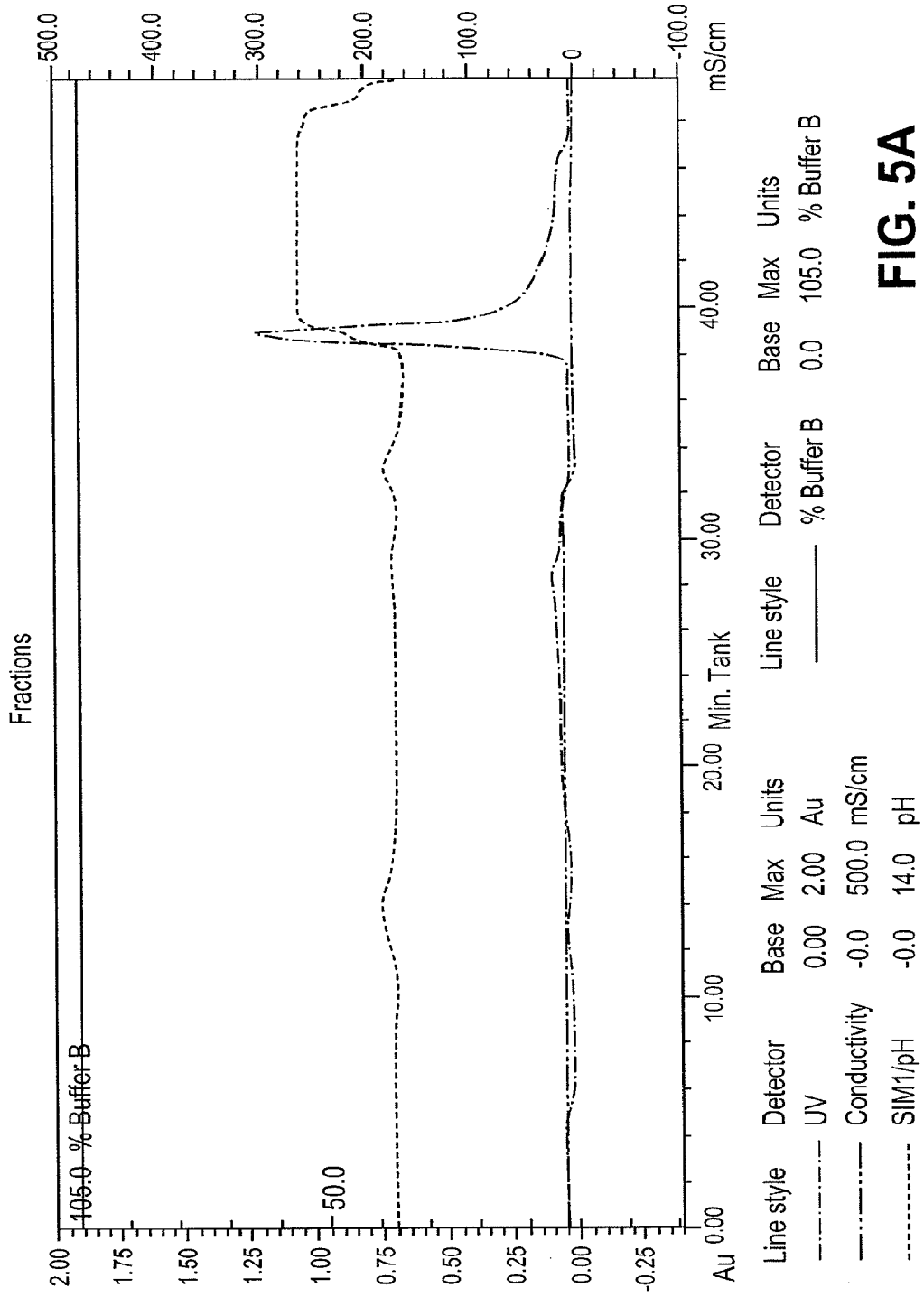
FIG. 5 is a chromatogram showing binding and elution of purified immunoglobulin from an acetylated phenylalanine UNOsphere resin as discussed in the Examples.
Figure 5B:
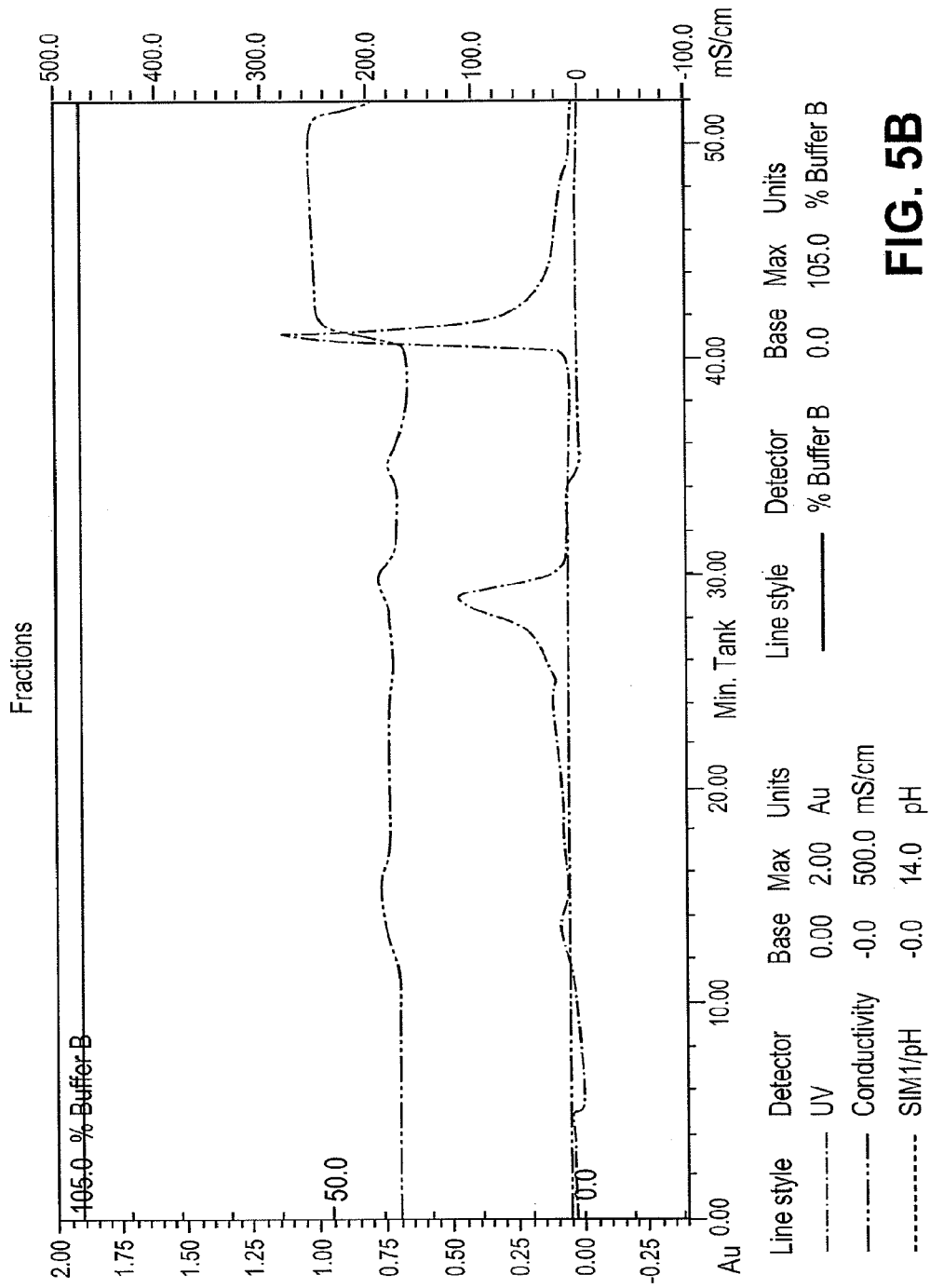

Purified immunoglobulin binding and elution was examined for UNOsphere Phenylalanine where the amine of the phenylalanine was, or was not, acetylated. FIGS. 4-5 shows that only a very small amount of IgG bound and eluted from non-acetylated UNOsphere Phenylalanine (FIG. 4) compared with that bound and eluted from acetylated UNOsphere Phenylalanine (FIG. 5) The top chromatogram in FIG. 5 represents UNOsphere Phenylalanine first solvent exchanged from water to acetone and then treated with acetyl chloride. The bottom chromatogram in FIG. 5 represents UNOsphere Phenylalanine in which the beads were vacuum dried and then acetylated with acetyl chloride.

Example 4

Phenylalanine Ligand—Hydrophobic Interaction Mode

Figure 6:
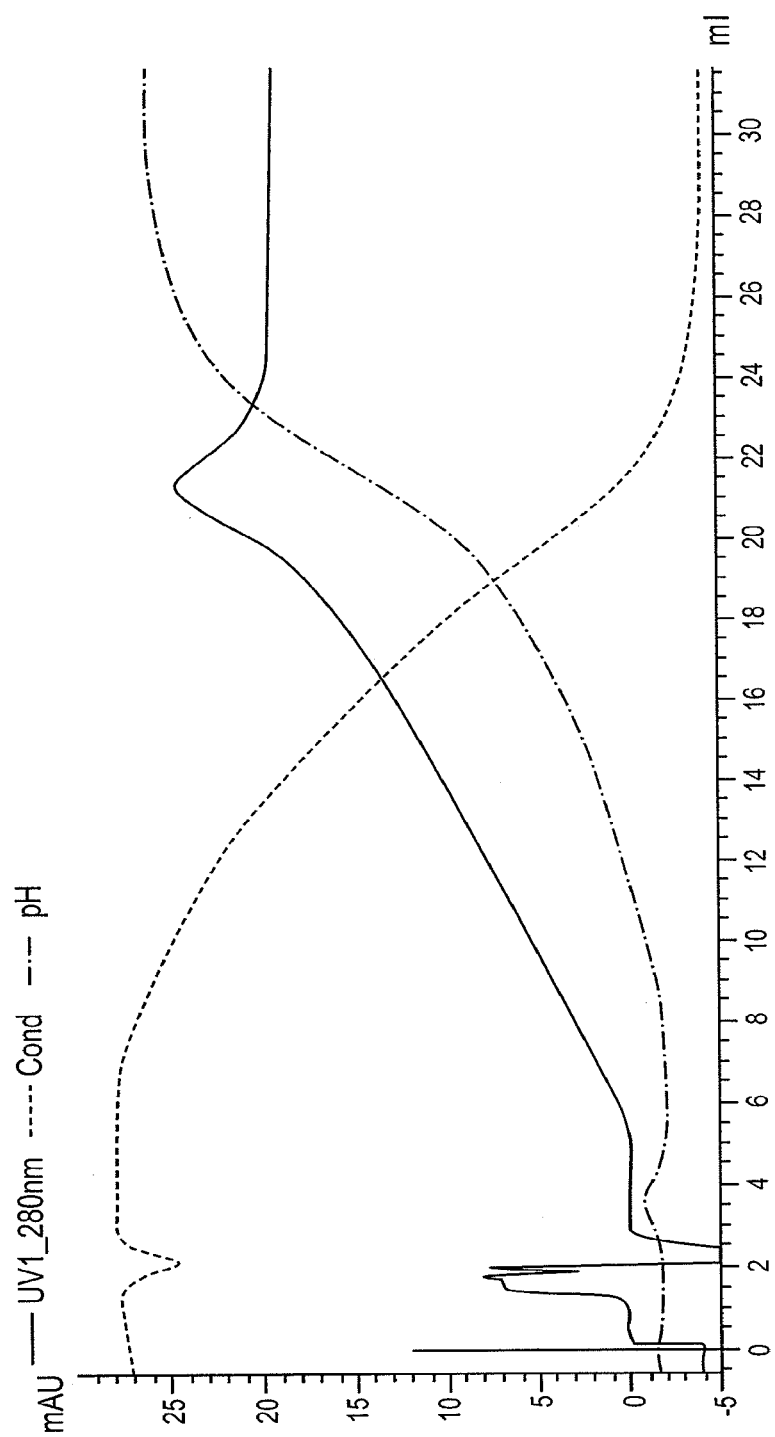
FIG. 6 is a chromatogram showing binding and elution being practiced in hydrophobic mode with a protein A purified monoclonal human IgG1. The column used comprised 1 mL UNOsphere Phenylalanine 5 mm×5 cm, 300 cm/hr. The column was equilibrated with buffer A (4M NaCl, 0.01M citate, 0.01M phosphate, pH 4.5) and 100 μL of the filtered unequilibrated sample was injected. The column was washed with ~2.5 column volumes (CV) of buffer A, and then eluted with 15CV linear gradient from 100% A to 100% B (Buffer B. 0.01M citrate, 0.01M phosphate, pH 7.5). The column was washed with B until equilibrium was reached with buffer B.

Another mode of the invention can be referred to as "hydrophobic interaction mode" because the phenylalanine column is operated by exploiting the phenyl group as a hydrophobic interaction group. This is illustrated in FIG. 6. In this experiment, the (Protein A-purified) antibody was loaded onto the UNOsphere Phenylalanine column in the presence of 4M NaCl. As the salt was washed out of the column (red trace), a pH gradient was initiated from 4.5-7.5 (light grey trace), which eluted the bound antibody (blue trace).

Example 5

T-Butyl Ester Derivative of Polymethacrylate

Macro-Prep epoxide base polymer is a polymethacrylate polymer produced from glycidyl methacrylate and diethylene glycol dimethacrylate crosslinker. Macro-Prep epoxide base bead does not contain a hydrophobic group; the hydrophobic group is introduced into the polymer in a post-polymerization reaction. Macro-Prep t-Butyl HIC resin is a mixed mode resin, produced by reaction of t-butanol and potassium t-butoxide with Macro-Prep Epoxide. During the t-butyl derivatization reaction, a small fraction of the ester groups on the polymer backbone are hydrolyzed to carboxylic acid groups, while t-butanol reacts with the pendent epoxide groups. Macro-Prep t-Butyl HIC typically contains from 131-266 micromoles carboxyl groups/ml and 25-45 micromoles t-butyl groups/ml resin. Unlike the integrated mixed mode ligand approach that we demonstrated using phenylalanine, the carboxyl groups are separated from the hydrophobic groups in Macro-Prep t-Butyl HIC. Macro-Prep t-Butyl HIC polymer is sufficiently porous to bind larger proteins, including immunoglobulins.

A monoclonal antibody cell culture filtrate was purified on the Macro Prep t-Butyl HIC resin under the following conditions. Chromatography conditions: T-Butyl HR 10/10 (8 mL of Macro-Prep t-Butyl HIC resin was packed in a 10 mm×10 cm chromatography column). The column was equilibrated with 25 mM acetate, pH 4.5, ~0.3 mS/cm 4 mL/min (300 cm/hr). To prepare the sample, it was diluted 1:1 with 25 mM acetate, titrated to pH 4.75, conductivity at about 11 mS/cm. A 100 mL sample was loaded and the column was subsequently washed with 25 mM acetate, pH 4.5. The flow rate was then reduced to 150 cm/hr (2 mL/min) and antibody was eluted with ten column volumes in a linear gradient to 10 mM citrate, 10 mM phosphate, pH ~7.5. (cond. about 4.6 mS/cm). Following elution, the column was stripped with 1M NaCl, then 1 M NaOH.

Figure 7:
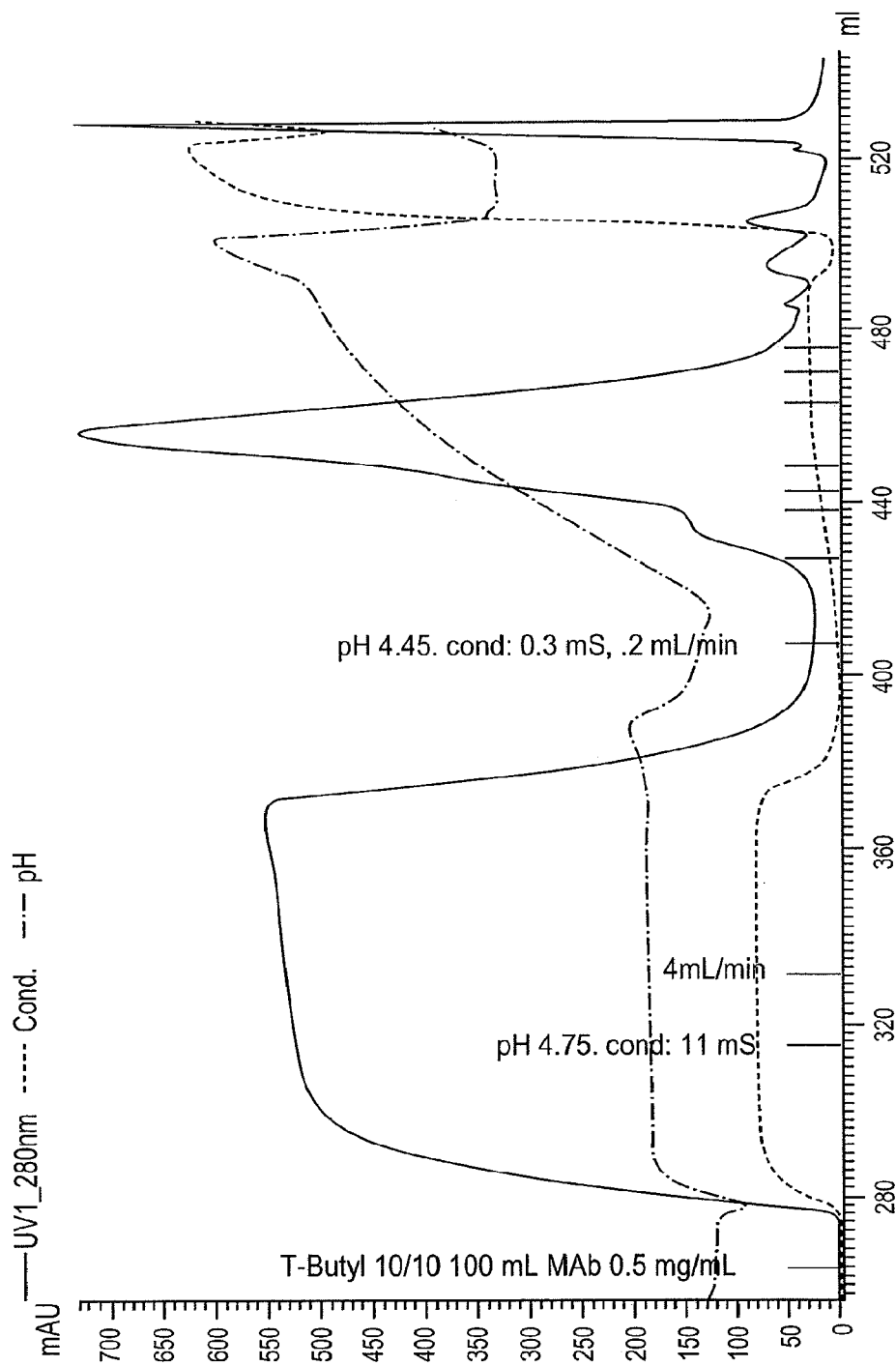
FIG. 7 is a chromatogram showing antibody capture from cell culture filtrate on Macro Prep t-Butyl HIC resin as discussed in the Examples.

A chromatogram illustrating chromatography of monoclonal antibody cell culture filtrate on Macro-Prep t-Butyl HIC is shown in FIG. 7. Fractions from the chromatograph were analyzed by SDS PAGE (FIG. 8). The antibody was efficiently captured on Macro-Prep t-Butyl HIC (no antibody bands in the unbound or wash fractions). Antibody eluted by pH gradient was well-purified and concentrated from the cell culture filtrate, without non-specific losses (no antibody detected in column strip fractions). The polyacrylamide gel electrophoresis pattern of the fractions (FIG. 8) is similar to that observed for the eluate from the phenylalanine column described above. These results on Macro-Prep t-Butyl HIC demonstrate that an integrated mixed mode ligand is not required for our mixed mode/CHT antibody purification method.

Based on our work described in examples above, chromatographic polishing of the pH-eluted antibody fraction from Macro-Prep t-Butyl HIC can be chromatographed on CHT, similar to the antibody pool eluted from phenylalanine mixed mode media, to further remove minor protein contaminants, antibody aggregates, DNA, and endotoxin.

Example 6

Hexanoic Acid Ligand

Figure 9:
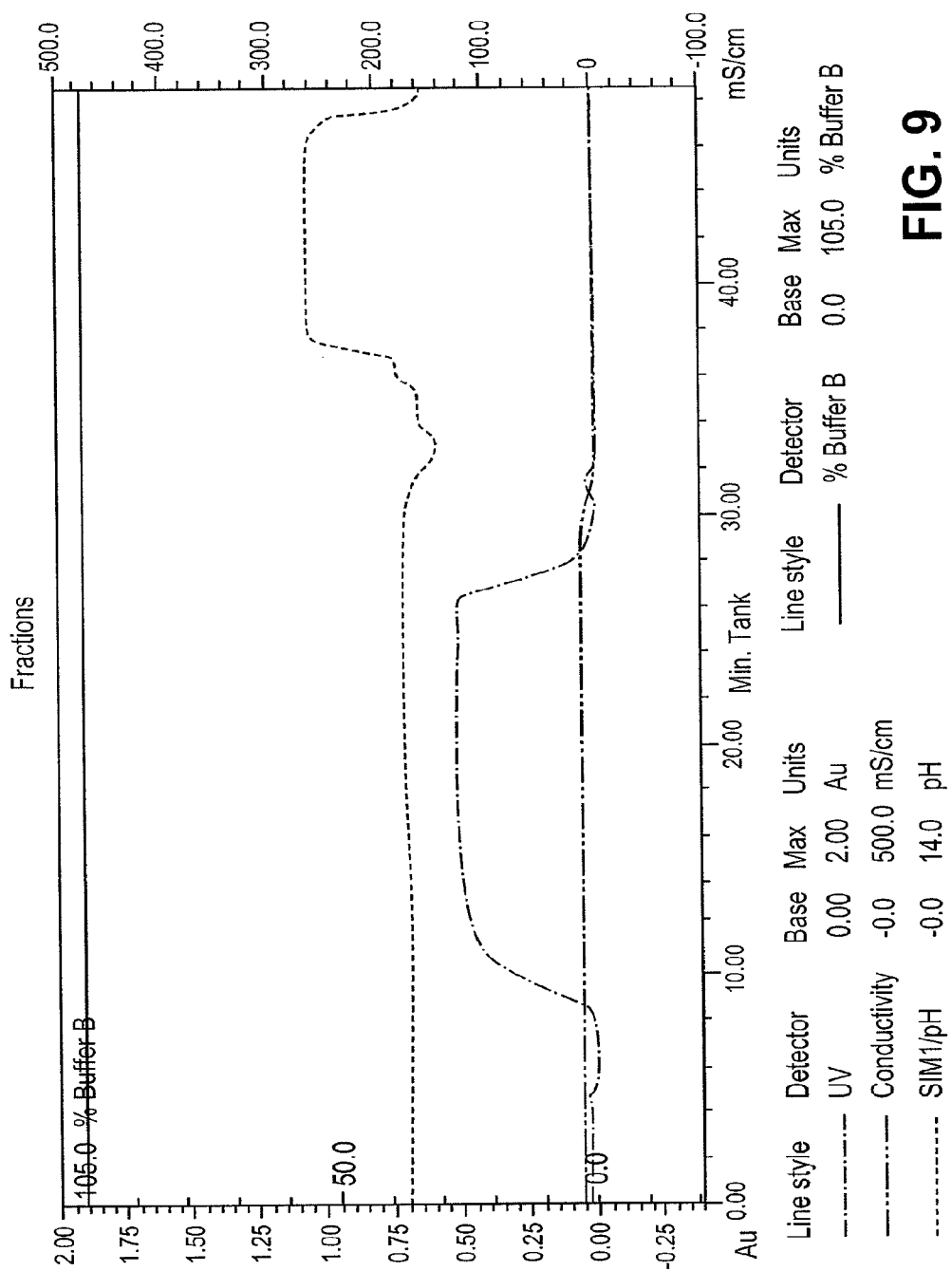
FIG. 9 is a chromatogram showing binding and elution of purified immunoglobulin from an amino caproic acid UNOsphere resin as discussed in the Examples.
Figure 10:
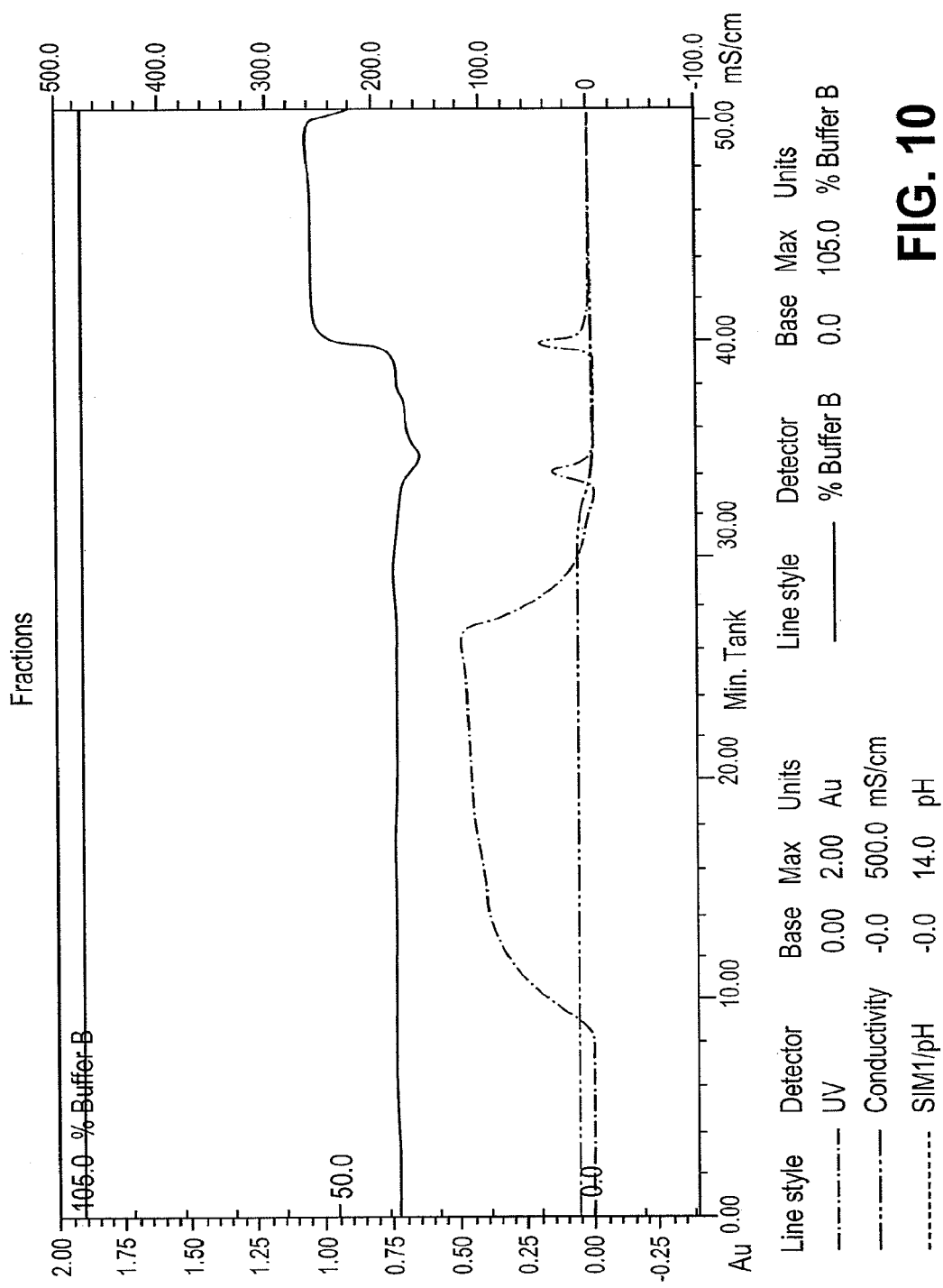
FIG. 10 is a chromatogram showing binding and elution of purified immunoglobulin from an acetylated amino caproic acid UNOsphere resin as discussed in the Examples.
Figure 11:
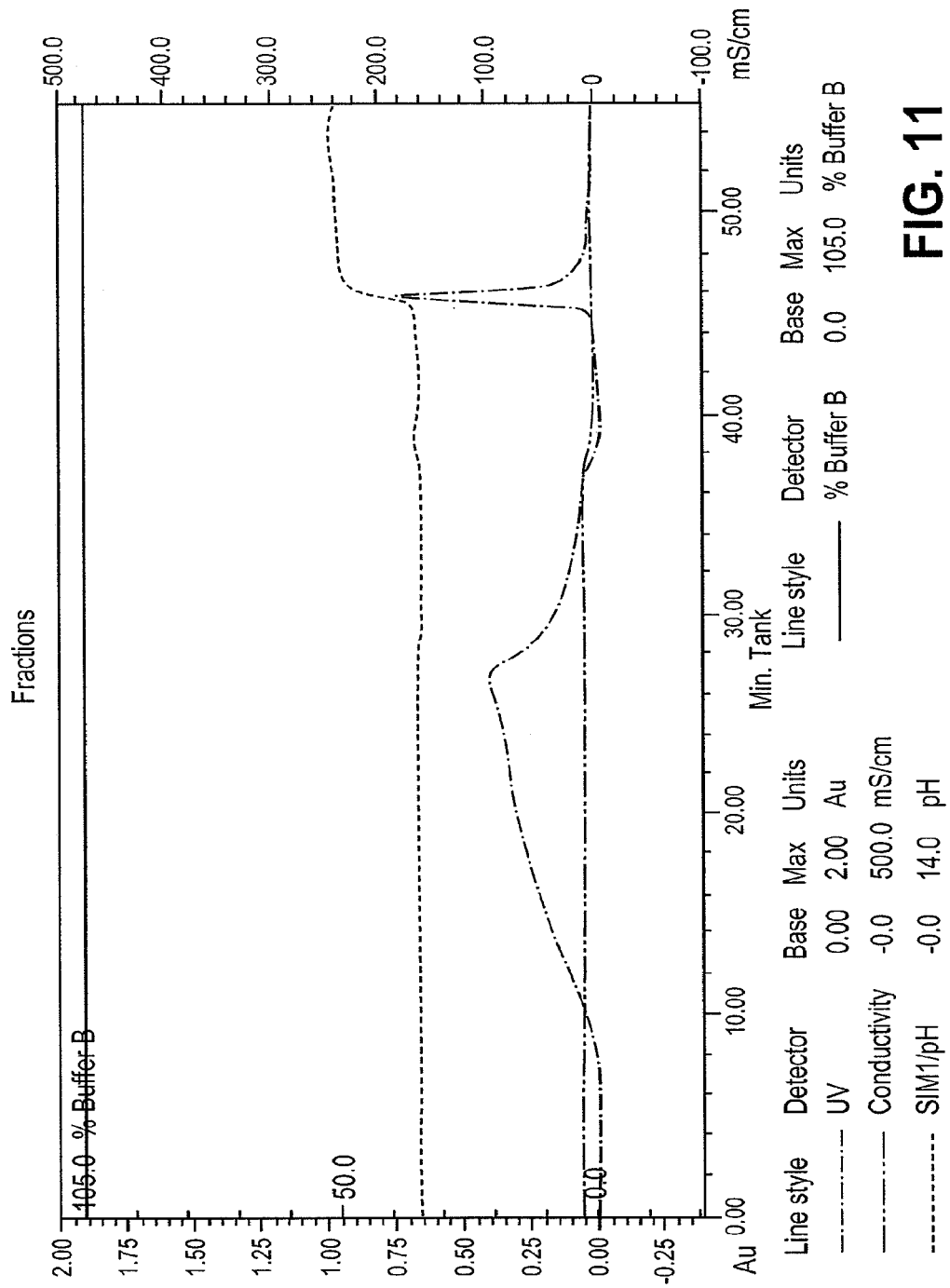
FIG. 11 is a chromatogram showing binding and elution of purified immunoglobulin from a hexanoic acid UNOsphere resin as discussed in the Examples.
Figure 12:
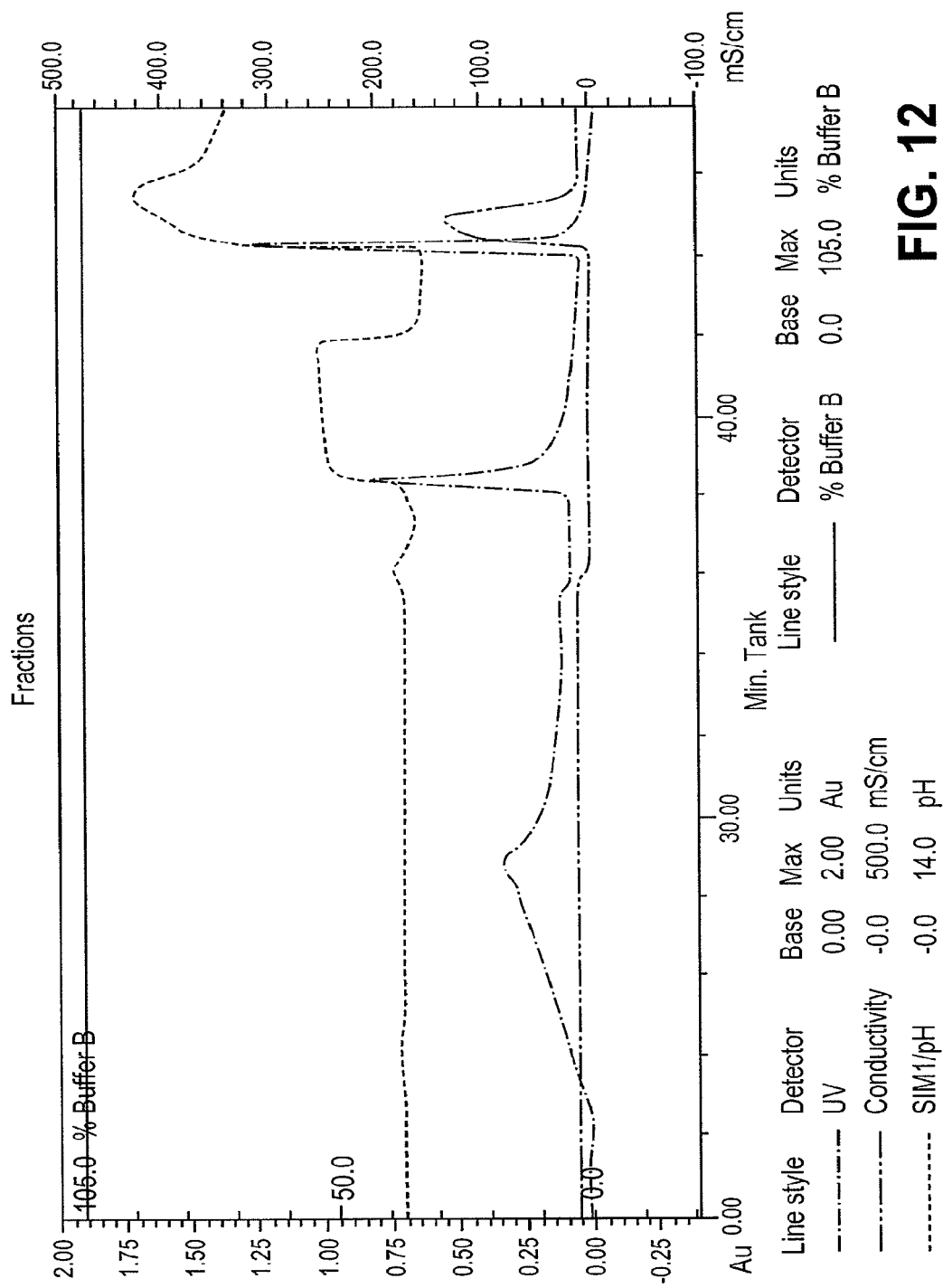
FIG. 12 is a chromatogram showing binding and elution of purified immunoglobulin from a hexanoic acid agarose resin as discussed in the Examples.
Figure 13:
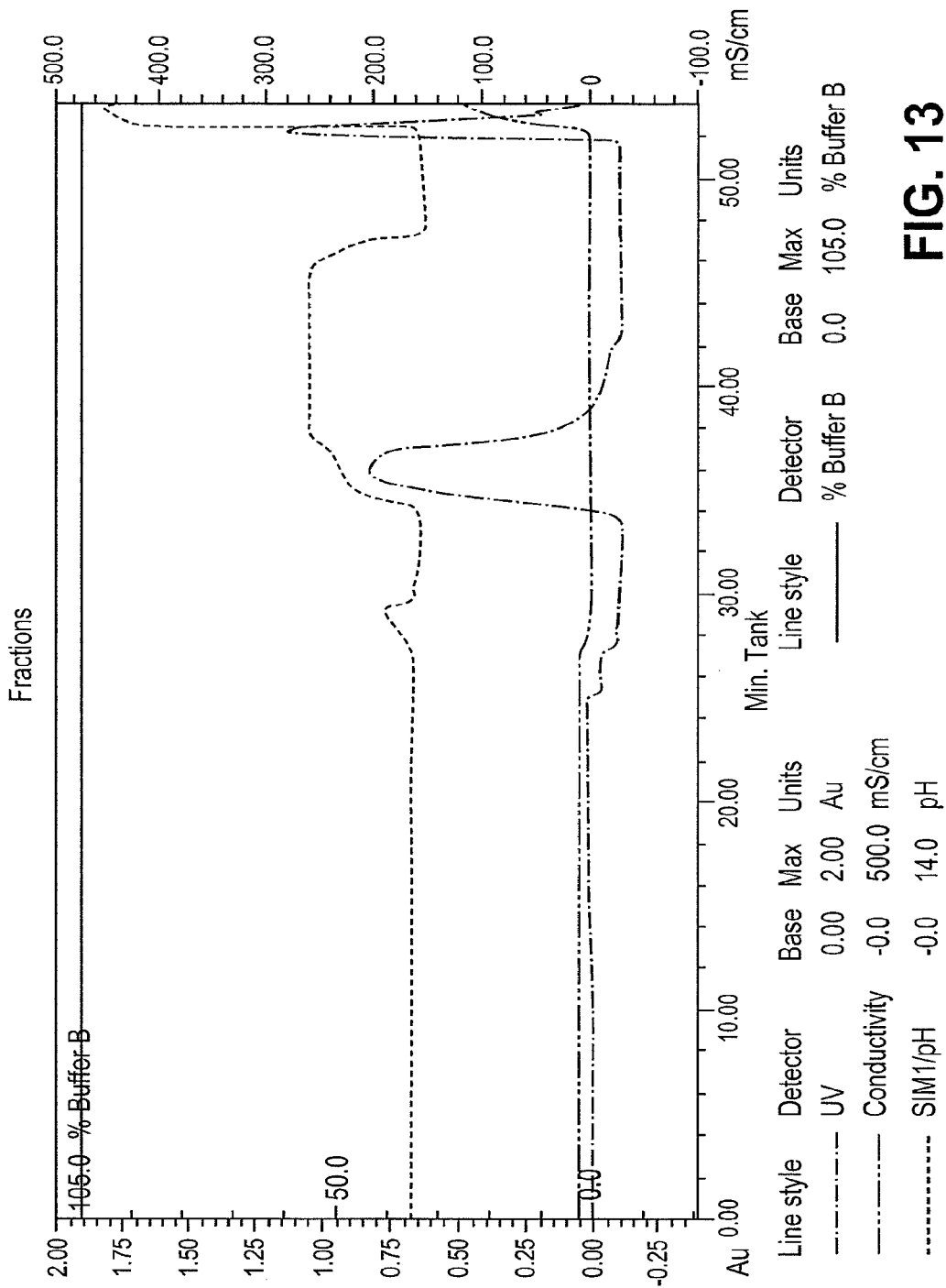
FIG. 13 is a chromatogram showing binding and elution of purified immunoglobulin from a hexanoic acid sepharose resin as discussed in the Examples.

Alkyl acids and amino alkyl acids were compared for their ability to purify antibodies. Aminocaproic acid was coupled to UNOsphere Diol by reductive amination (similar reaction to the phenylalanine coupling). No IgG binding was detected in our purified IgG uptake assay (FIG. 9). Acetylation of this material demonstrated only a slight uptake and release of purified IgG in our assay (FIG. 10). By contrast, coupling bromohexanoic acid to UNOsphere Diol provides IgG binding with a sharply eluted peak upon pH shift (FIG. 11). When bromohexanoic acid was coupled similarly to agarose (Sterogene Ultraflow, FIG. 12) or to GE agarose (Sepharose 4B, FIG. 13), Sterogene agarose gave a profile very similar to that of UNOsphere hexanoic acid, while Sepharose 4B showed much higher IgG binding with pH-based elution.

There are subtle differences between aminocaproic acid and bromohexanoic acid [—H$_2$N(CH$_2$)$_5$COOH] vs. [Br(CH$_2$)$_5$COOH], when coupled to hydroxyl groups on polymers, which result in significant differences in IgG binding properties. This effect was not anticipated, based on previous work. Lihme (U.S. Pat. No. 6,498,236), used a variety of activated spacer groups including epichlorohydrin, allyl glycidyl ether, bis-epoxides and glutaric dialdehyde. Burton (U.S. Pat. No. 5,652,348) used a variety of activated groups for coupling amines. Some produced uncharged amide linkages, but others including epoxide, cyanogen bromide, tosyl, divinylsulfone produced a secondary amine derivative which would give a positive charge at acidic pH's. Without intending to be bound by any theory of operation, we hypothesize the difference is due to protonation of the secondary amine nitrogen, forming a zwitterion at low pH, which would repel the (positively charged) IgG molecule from the bead at acidic pH's, conditions where the carboxyl group is largely protonated (and uncharged). Acetylation or other "capping" of the amine nitrogen would eliminate the ability to protonate the amine to form a zwitterion, for both aminocaproic acid and phenylalanine Example 7

Additional Mixed Mode Matrix

Figure 14:
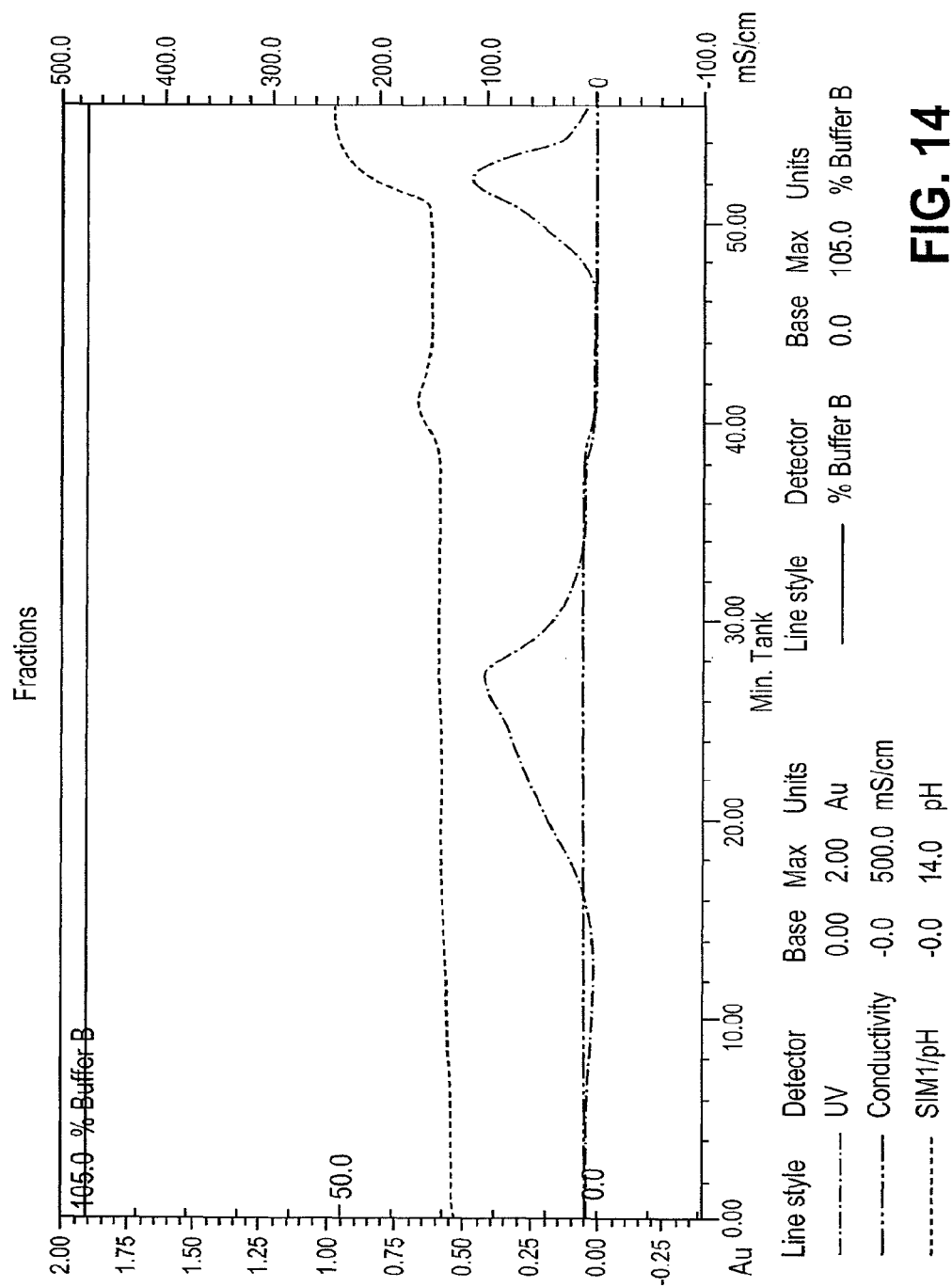
FIG. 14 is a chromatogram showing binding and elution of purified immunoglobulin from a phenyl derivative of UNOsphere diol resin containing carboxyl groups as discussed in the Examples.
Figure 15:
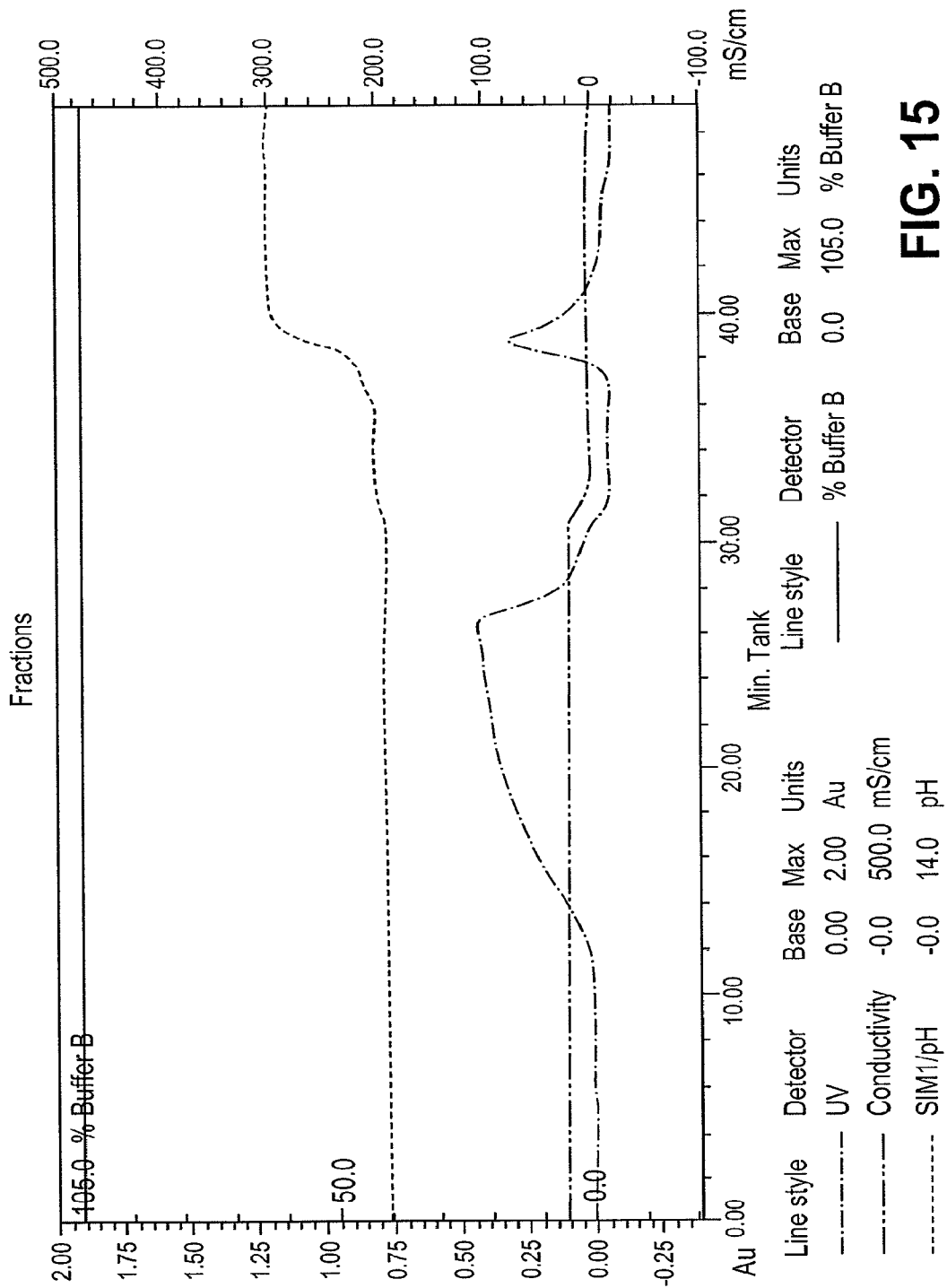
FIG. 15 is a chromatogram showing binding and elution of purified immunoglobulin from a Macro Prep t-Butyl HIC resin as discussed in the Examples.

An UNOsphere Diol polymer with a carboxyl group in the backbone of the polymer was produced, then derivatized this bead with phenyl groups, to create a material with separate hydrophobic and ionic groups, somewhat like the Macro-Prep t-Butyl HIC polymer. FIG. 14 is a purified IgG binding chromatogram for this material. The elution profile of the IgG is slightly different from that of media containing a single ligand comprised of both the weak acid and hydrophobic group. For this media, where the acid and hydrophobic groups are not necessarily in close proximity, there is a broader elution profile for IgG, beginning even before the pH gradient trace rises. For comparison, the IgG binding/elution profile for Macro-Prep t-Butyl HIC is shown in FIG. 15.

All references cited herein are incorporated by reference in their entirety and for all purposes to the same extent as if each individual publication or patent or patent application was specifically and individually indicated to be incorporated by reference in its entirety for all purposes. To the extent publications and patents or patent applications incorporated by reference contradict the disclosure contained in the specification, the specification is intended to supercede and/or take precedence over any such contradictory material.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with the true scope and spirit of the invention being indicated by the following claims.

What is claimed is:

1. A method for purifying antibodies from a solution containing antibodies, the method comprising
   a. contacting a first solution containing antibodies to a mixed mode chromatography matrix comprising an n-alkyl acid comprising 2-10 carbons, wherein the n-alkyl acid is linked directly to a hydroxy-functionalized solid support, thereby binding at least a portion of the antibodies to the matrix;
   b. separating the matrix with bound antibodies from the first solution;
   c. eluting the bound antibodies by raising the pH of a solution in contact with the matrix and bound antibodies to pH 6-8, thereby producing an elution solution at pH 6-8 comprising eluted antibodies;
   d. contacting the elution solution comprising eluted antibodies to a solid support matrix, the solid support matrix comprising hydroxyapatite (HT) or fluorapatite (FT), wherein at least a portion of the antibodies bind to the solid support matrix;
   e. separating the solid support matrix and bound antibodies from the elution solution; and
   f. eluting the bound antibodies from the solid support matrix, thereby purifying the antibodies from the solution.

2. The method of claim 1, wherein the elution solution of eluted antibodies is not substantially changed before the contacting of the elution solution.

3. The method of claim 1, wherein the contacting (a.) comprises binding the antibodies to the mixed mode chromatography matrix at a pH below 7.

4. The method of claim 3, wherein the mixed mode chromatography matrix comprises charged moieties at a pH below 7.

5. The method of claim 1, wherein the contacting (a.) comprises binding the antibodies to the mixed mode chromatography matrix in the presence of at least 1 M salt.

6. The method of claim 1, wherein the contacting (a.) comprises binding the antibodies to the mixed mode chromatography matrix in the presence of 1 M or less salt.

7. The method of claim 1, wherein the eluting (c.) comprises raising the pH from below pH 7 to a pH above pH 7.

8. The method of claim 1, wherein the solid support matrix comprises ceramic hydroxyapatite (CHT).

9. The method of claim 1, wherein the solid support matrix comprises ceramic fluorapatite (CFT).

10. The method of claim 1, wherein the eluting (c.) comprises eluting the bound antibodies by raising the pH of the solution in contact with the mixed mode chromatography matrix and bound antibodies to about pH 7.

11. The method of claim 1, wherein the eluting (c.) comprises eluting the bound antibodies by raising the pH of the solution in contact with the mixed mode chromatography matrix and bound antibodies to about pH 7.2.

12. The method of claim 1, wherein the solution in contact with the mixed mode chromatography matrix during the eluting has less than 50 mM salt.

13. The method of claim 12, wherein the salt is selected from the group consisting of sodium phosphate, sodium acetate, potassium phosphate, and potassium acetate.

14. A method for purifying antibodies from a solution containing antibodies, the method comprising
   a. contacting a first solution containing antibodies to a mixed mode chromatography matrix, wherein the mixed mode chromatography matrix comprises an n-alkyl acid comprising 2-10 carbons, wherein the n-alkyl acid is linked directly to a hydroxy-functionalized solid support, thereby binding at least a portion of the antibodies to the matrix;

b. separating the matrix with bound antibodies from the first solution;

c. eluting the bound antibodies by changing the pH or salt concentration of solution in contact with the matrix and bound antibodies, thereby producing a solution comprising eluted antibodies and purifying antibodies from a solution containing antibodies.

15. The method of claim 14, wherein the n-alkyl acid is selected from the group consisting of butanoic acid, hexanoic acid, octanoic acid, and decanoic acid.

* * * * *